United States Patent
King et al.

(10) Patent No.: US 12,115,198 B2
(45) Date of Patent: Oct. 15, 2024

(54) MICROBIALS FOR ANIMALS

(71) Applicants: MICROBIAL DISCOVERY GROUP, LLC, Franklin, WI (US); UNITED ANIMAL HEALTH, INC., Sheridan, IN (US)

(72) Inventors: Michael R. King, Oak Creek, WI (US); Sona Son, Cudahy, WI (US); Elizabeth Galbraith, Wauwatosa, WI (US); Samanta R. Fensterseifer, Byron, MI (US); Ricardo P. Arias, Byron, MI (US)

(73) Assignees: ·MICROBIAL DISCOVERY GROUP, LLC, Franklin, WI (US); UNITED ANIMAL HEALTH, INC., Sheridan, IN (US)

( * ) Notice: Subject to any disclaimer, the term of this patent is extended or adjusted under 35 U.S.C. 154(b) by 0 days.

(21) Appl. No.: 16/590,569

(22) Filed: Oct. 2, 2019

(65) Prior Publication Data

US 2020/0138877 A1    May 7, 2020

Related U.S. Application Data

(60) Provisional application No. 62/740,169, filed on Oct. 2, 2018.

(51) Int. Cl.
| | |
|---|---|
| A61K 35/742 | (2015.01) |
| A23K 10/18 | (2016.01) |
| A23K 20/189 | (2016.01) |
| A23K 20/195 | (2016.01) |
| A23K 50/10 | (2016.01) |
| A23K 50/30 | (2016.01) |
| A61K 9/00 | (2006.01) |
| A61K 35/741 | (2015.01) |
| A61K 45/06 | (2006.01) |
| A61P 3/00 | (2006.01) |
| A61K 35/00 | (2006.01) |

(52) U.S. Cl.
CPC ............ *A61K 35/742* (2013.01); *A23K 10/18* (2016.05); *A23K 20/189* (2016.05); *A23K 20/195* (2016.05); *A23K 50/10* (2016.05); *A23K 50/30* (2016.05); *A61K 9/0056* (2013.01); *A61K 9/0095* (2013.01); *A61K 35/741* (2013.01); *A61K 45/06* (2013.01); *A61P 3/00* (2018.01); *A61K 2035/115* (2013.01)

(58) Field of Classification Search
CPC .. A61K 35/742; A61K 9/0095; A61K 9/0056; A23K 20/189; A23K 20/195; A23K 50/10; A23K 50/30; A23K 50/20; A23K 50/75; A23K 10/18; A23K 50/40
See application file for complete search history.

(56) References Cited

U.S. PATENT DOCUMENTS

| | | |
|---|---|---|
| 4,673,638 A | 6/1987 | Grosch et al. |
| 5,587,475 A | 12/1996 | Helquist et al. |
| 5,589,381 A | 12/1996 | Neyra et al. |
| 5,665,354 A | 9/1997 | Neyra |
| 6,268,147 B1 | 7/2001 | Beattie |
| 7,754,469 B2 | 7/2010 | Baltzley et al. |
| 7,807,185 B2 | 10/2010 | Farmer |
| 8,025,874 B2 | 9/2011 | Bellot et al. |
| 8,540,981 B1 | 9/2013 | Wehnes et al. |
| 9,175,258 B2 | 11/2015 | Bywater-Ekegard |
| 9,410,213 B2 | 8/2016 | Matheny |
| 9,758,414 B2 | 9/2017 | Dash et al. |
| 10,961,275 B2 | 3/2021 | Bralkowski et al. |
| 2001/0027947 A1 | 10/2001 | Tsuchiya |
| 2005/0255092 A1 | 11/2005 | Rehberger et al. |
| 2005/0266468 A1 | 12/2005 | Bedzyk |
| 2006/0188978 A1 | 8/2006 | Grant |
| 2008/0050774 A1 | 2/2008 | Berka |
| 2009/0280090 A1 | 11/2009 | Rehberger et al. |
| 2010/0010080 A1 | 1/2010 | Mockett et al. |
| 2010/0062021 A1 | 3/2010 | Winkelman |
| 2010/0092428 A1 | 4/2010 | Schmidt et al. |
| 2010/0291564 A1 | 11/2010 | Stanley |
| 2012/0100118 A1 | 4/2012 | Rehberger et al. |
| 2012/0015259 A1 | 12/2012 | Friedlander et al. |

(Continued)

FOREIGN PATENT DOCUMENTS

| | | |
|---|---|---|
| CN | 101159102 | 4/2008 |
| CN | 103980535 | 8/2014 |

(Continued)

OTHER PUBLICATIONS

Mapleton. About our Cows—Producing Milk & Pregnancy. Mapleton's Organic. 2016;1-3.*
Crawford E. Good Nutrition Vital for Pregnant Cows. NDSU. 2016;1.*
Karigar et al., "Role of Microbial Enzymes in the Bioremediation of Pollutants: A Review," Enzyme Research, vol. 2011, Article ID 805187, 11 pages.
Schmidt et al., "New Concepts of microbial treatment processes for the nitrogen removal in wastewater," 2003.

(Continued)

*Primary Examiner* — Lynn Y Fan
(74) *Attorney, Agent, or Firm* — Barnes & Thornburg

(57) ABSTRACT

The invention relates to direct-fed microbials for use in improving reproductive performance in animals, decreasing death loss and/or off-feed events in animals, improving milk production and/or milk quality in dairy animals, and inhibiting a disease or disorder in dairy animals selected from the group consisting of milk fever, ketosis, retained placenta, metritis, pneumonia, and displaced abomasum. More particularly, the invention relates to isolated *Bacillus* strains 86, 300, 101, 235, 177, and 102, and strains having all of the identifying characteristics of these strains, for uses comprising the above-mentioned uses.

15 Claims, 6 Drawing Sheets

Specification includes a Sequence Listing.

(56) References Cited

U.S. PATENT DOCUMENTS

| | | |
|---|---|---|
| 2012/0315258 A1 | 12/2012 | Rehberger et al. |
| 2012/0315259 A1 | 12/2012 | Friedlander et al. |
| 2013/0064927 A1 | 3/2013 | Davis et al. |
| 2013/0098837 A1 | 4/2013 | Dash |
| 2013/0100118 A1 | 4/2013 | Mlyniec et al. |
| 2013/0136695 A1 | 5/2013 | Hargis et al. |
| 2013/0216586 A1 | 8/2013 | LeBrun et al. |
| 2013/0295067 A1 | 11/2013 | Baltzley et al. |
| 2014/0106974 A1 | 4/2014 | Sun et al. |
| 2014/0141044 A1 | 5/2014 | Dana-Farber |
| 2014/0273150 A1 | 9/2014 | Angel |
| 2014/0315716 A1 | 10/2014 | Matheny |
| 2014/0363819 A1 | 12/2014 | Rowlyk |
| 2015/0079058 A1 | 3/2015 | Nielsen et al. |
| 2015/0111214 A1 | 4/2015 | Liu |
| 2015/0147303 A1 | 5/2015 | Hsieh |
| 2015/0216203 A1 | 8/2015 | Isaksen et al. |
| 2015/0216916 A1 | 8/2015 | Galbraith et al. |
| 2016/0108467 A1 | 4/2016 | Semikhodskii et al. |
| 2017/0079308 A1 | 3/2017 | King et al. |
| 2017/0166466 A1 | 6/2017 | King et al. |
| 2017/0246224 A1 | 8/2017 | King et al. |
| 2017/0327840 A1 | 11/2017 | Bayer |
| 2018/0361444 A1 | 12/2018 | Franssen |
| 2019/0021341 A1 | 1/2019 | Davis et al. |
| 2020/0015497 A1 | 1/2020 | King et al. |
| 2020/0029592 A1 | 1/2020 | King et al. |
| 2020/0093158 A1 | 3/2020 | Calabotta et al. |

FOREIGN PATENT DOCUMENTS

| | | |
|---|---|---|
| CN | 107841478 | 3/2018 |
| CN | 109497281 | 3/2019 |
| EP | 1574564 | 9/2005 |
| GB | 1392813 | 4/1975 |
| GB | 1434582 | 5/1976 |
| JP | 3417904 | 6/2003 |
| KR | 100427600 | 4/2004 |
| WO | 2007083147 | 7/2007 |
| WO | 2010/0033714 | 3/2010 |
| WO | 2010032233 | 3/2010 |
| WO | 2012/009712 | 1/2012 |
| WO | 2012101528 | 8/2012 |
| WO | 2014/020141 | 2/2014 |
| WO | 2014/067081 | 5/2014 |
| WO | 20140172520 | 10/2014 |
| WO | 2015057330 | 4/2015 |
| WO | 2015/160960 | 10/2015 |
| WO | 2015/175667 | 11/2015 |
| WO | 2017/081105 | 5/2017 |
| WO | 2017/151608 | 9/2017 |
| WO | 2018/148847 | 8/2018 |
| WO | 2019090068 | 5/2019 |
| WO | 2019090088 | 5/2019 |
| WO | 2019/141815 | 7/2019 |
| WO | 2019/152791 | 8/2019 |
| WO | 2019/213243 | 11/2019 |
| WO | 2020072578 | 4/2020 |
| WO | 2021035137 | 2/2021 |
| WO | 2021041603 | 3/2021 |
| WO | 2023018686 | 2/2023 |

OTHER PUBLICATIONS

Ramachandran et al., "A Broad-Spectrum Antimicrobial Activity of Bacillus subtilis RLID 12.1," 2014.

Kiarie et al. "The Role of Added Feed Enzymes in Promoting Gut Health in Swine and Poultry," Nutrition Research Reviews, Jun. 1, 2013 (Jun. 1, 2013), vol. 26, pp. 71-88.

La Ragione et al. "Bacillus subtilis Spores Competitively Exclude Escherichia coli O78: K80 in Poultry," Veterinary Microbiology, Mar. 20, 2001 (Mar. 20, 2001). vol. 79, pp. 133-142.

Harnentis et al. "Isolation, Characterization and Production of Mannanase from Thermophilic Bacteria to Increase the Feed Quality," Pakistan Journal of Nutrition 12 (4): 360-364, 2013.

PCT Search Report and Written Opinion for PCT/US2015/030578, completed Jul. 9, 2015.

Extended European Search Report, European Application No. 15792802.9-1358 dated Nov. 8, 2017, 8 pages.

Souza et al. J. Anim. Sci. vol. 90, Suppl. 3/J. Dairy Sci. vol. 95, Suppl. 2 T281.

Credille et al. (2014). Prevalence of bacteremia in dairy cattle with acute puerperal metritis. J Vet Intern Med, 28:1606-1612.

Sheldon et al. (2009). Defining postpartum uterine disease and the mechanisms of infection and immunity in the female reproductive tract in cattle. Biol Reprod 81:1025-1032.

Abutarbush et al. (2005). Jejunal hemorrhage syndrome in dairy and beef cattle: 11 cases (2001 to 2003). Can. Vet. J. Rev. Vét. Can. 46, 711-715.

Abutarbush et al. (2004). Jejunal hemorrhage syndrome in 2 Canadian beef cows. Can. Vet. J. 45, 48-50.

Adaska et al. (2014). Jejunal hematoma in cattle: a retrospective case analysis. J. Vet. Diagn. Investig. Off. Publ. Am. Assoc. Vet. Lab. Diagn. Inc 26, 96-103.

Baines et al. (2011). Mouldy feed, mycotoxins and Shiga toxin—producing Escherichia coli colonization associated with Jejunal Hemorrhage Syndrome in beef cattle. BMC Vet. Res. 7, 24.

Ceci, L., Paradies, P., Sasanelli, M., De Caprariis, D., Guarda, F., Capucchio, M. t., and Carelli, G. (2006). Haemorrhagic Bowel Syndrome in Dairy Cattle: Possible Role of Clostridium perfringens Type A in the Disease Complex. J. Vet. Med. Ser. A 53, 518-523.

Dennison et al. (2002). Hemorrhagic bowel syndrome in dairy cattle: 22 cases (1997-2000). J. Am. Vet. Med. Assoc. 221, 686-689.

Dennison et al. (2005). Comparison of the odds of isolation, genotypes, and in vivo production of major toxins by Clostridium perfringens obtained from the gastrointestinal tract of dairy cows with hemorrhagic bowel syndrome or left-displaced abomasum. J. Am. Vet. Med. Assoc. 227, 132-138.

Malinen et al. (2003). Comparison of real-time PCR with SYBR Green I or 5'-nuclease assays and dot-blot hybridization with rDNA-targeted oligonucleotide probes in quantification of selected faecal bacteria. Microbiology. 149:269-277.

West et al. (2007) Rapid Detection of Escherichia coli Virulence Factor Genes using Multiplex Real-Time TaqMan® PCR Assays. Veterinary Microbiology 122(3-4): 323-331.

Frydendahl et al. (2001). Automated 5' nuclease assay for detection of virulence factors in porcine Escherichia coli. Molec.Cell. Probes. 15: 151-160.

Nielsen et al. (2003). Detection and characterization of verocytotoxin-producing Escherichia coli by automated 5 nuclease PCR assay, Journal of ClinicalMicrobiology, vol. 41, No. 7, pp. 2884-2893.

Jinneman et al. (2003). Multiplex Real-Time PCR Method to Identify Shiga Toxin Genes stx1 and stx2 and Escherichia coli O157:H7/H—Serotype. Appl. Environ. Microbiol. Oct. 2003 vol. 69 No. 10 6327-6333.

Yatsuyanagi et al. (2002). Characterization of enteropathogenic and enteroaggregative Escherichia coli isolated from diarrheal outbreaks, Journal of Clinical Microbiology, vol. 40, No. 1, pp. 294-297.

Albini et al. (2010). Real-time multiplex PCR assays for reliable detection of Clostridium perfringens toxin genes in animal isolates, Veterinary Microbiology, 127 (1-2): 179-185.

Johnson et al. (2012). A MIQE-Compliant Real-Time PCR Assay for Aspergillus Detection., PLOSone., 7(7): 1-8.

International search report and written opinion for PCT/US2018/058948, mailed Jan. 18, 2019.

Miller et al., "Sanitary Landfill Simulation: Test Parameters and a Simulator Conceptual Design," Naval Facilities Engineering Command: Civil Engineering Laboratory, Oct. 20, 1976 (Oct. 20, 1976), pp. 1-47. Retrieved from the Internet: <https://apps.dtic.mil/dtic/tr/fulltext/u2/a030998.pdf>.

Fei et al., "A laboratory landfill simulator for physical, geotechnical, chemical and microbial characterization of solid waste biodegradation processes," Couples Phenomena in Environmental Geotechnics, May 20, 2013 (May 30, 2013), Taylor & Francis Group, London, pp. 321-327.

(56) References Cited

OTHER PUBLICATIONS

Mahar et al., "Modeling and simulation of landfill gas production from pretreated MSW landfill simulator," Frontiers of Environmental Science & Engineering, Apr. 15, 2014 (Apr. 15, 2014), vol. 10, Iss. 1, pp. 159-167.
International search report for PCT/US2019/054190, Feb. 10, 2020.
Canning, et al., "Effect of direct-fed microbial Bacillus subtilis C-3102 on enteric health in nursery pigs after challenge with porcine epidemic diarrhea virus," Journal of Swine Health and Production, May 3, 2017, 25(3): 129-137.
Peng, et al., "Evaluation of antiviral activity of Bacillus licheniformis-fermented products against porcine epidemic diarrhea virus," AMB Express, Dec. 3, 2019, 9(191): 1-12.
Bae H.D., Yanke L.J, Cheng K.J., Selinger L.B., 1999, "A novel staining method for detecting phytase activity," Journal of Microbiological Methods, 39:1, 17-22.
Zganjer, et al. Treatment of rectal prolapse in children with cow milk injection sclerotherapy: 30-year experience, World Journal of Gastroanterology, 2008, 14(5) 740-7.
Rajendram et al., Journal of Microbiological Methods, 2006, 67, 582-92.
Krishnani, Genbank entry KJ000877 published Feb. 2014.
Lowe, et al., Nucleic Acids Research, 1990, 18(7) 1757-61.
McClure et al. "Assessment of DNA extracted from FTA® cards for use on the Illumina iSelect Beach Chip," BMC Research Notes, 2009, 2(107) 4 pages.
Haldar et al., Development of a haemolysin gene-based multiplex PCR for simultaneous detection of Vibrio.
Campbelli, Vibrio harveyi and Vibrio parahaemolyticus, Letters in Applied Microbiology, 2010, 50, 146-52.
EP Search report in EP 16789853 completed Aug. 8, 2018.
International Search Report prepared for PCT/US2020/048101 mailed Jan. 22, 2021.
International search report and written opinion for PCT/US2017/019941, mailed May 26, 2017.
International search report for PCT/US2020/047390, mailed Jan. 21, 2021.
Sonune et al. "Isolation, characterization and identification of extracellular enzyme producer Bacillus licheniformis from municipal wastewater and evaluation of the biodegradability," Biotechnology Research and Innovation, Jan.-Dec. 2018, vol. 2, No. 1 pp. 37-44.
Safitri et al. "Ability of Bacterial Consortium: *Bacillus coagulans, Bacilus licheniformis, Bacillus pumilus, Bacillus subtilis, Nitrosomonas* sp. and *Pseudomonas putida* in Bioremediation of Waste Water in Cisirung Waste Water Treatment Plant," Agrolife Scientific Journal, 2015, vol. 4, No. 1, pp. 146-152.
Ou et al. "Identification of HIV-1 infected infants and young children using real-time RT PCR and dned blood spots rom Uganda and Cameroon," Journal of Virological Methods, 2007, 144, 109-14.
Dobbs et al , 2002 Arch Pathol Lab Med. vol. 126, p. 56-63.
Chen et al, 2013 J of Proteone Research, 12, p. 1151-1161.
International search report and written opinion for PCT/US2019/030182, mailed Aug. 8, 2019.
Choudhary et al 2009 (interactions of *Bacillus* supp. and plants—with special reference to induced systemic resistance (ISR): Microbiologial Research 164: 493-513).
International search report and written opinion for PCT/US2020/023586, mailed May 20, 2020.
Sumi et al, Antimicrobial peptides of the genus *Bacillus*: a new era for antibiotics, Nov. 19, 2014, p. 1-7.
EPA, Final Risk assessment of Bacillus Subtilis, Feb. 1997, p. 3, 9 (1997).
European Search Report, European Application No. 20855232.3-1105 dated Aug. 31, 2023, 8 pages.
Supp. European Search Report, European Application No. 20858946, dated Aug. 23, 2023.
Sonune et al., "Isolation, characterization and identification of extracellular enzyme producer Bacillus licheniformis from municipal wastewater and evaluation of their biodegradability." Biotechnology Research and Innovation, vol. 2, No. 1, Jan. 1, 2018, pp. 37-44.
Cohn et al., "Bacillus Strains Improving Health and Performance of Production Animals." IP.com, ip.com Inc., Feb. 11, 2016, p. 36, line 54.

\* cited by examiner

SEQUENCE LISTING

```
<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggtgcgggaa                                                               10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtttcgctcc                                                               10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtagacccgt                                                               10
```

MICROBIALS FOR ANIMALS

CROSS-REFERENCE TO RELATED APPLICATIONS

This application claims priority under 35 U.S.C. § 119(e) to U.S. Provisional Application Ser. No. 62/740,169 filed on Oct. 2, 2018, the entire disclosure of which is incorporated herein by reference.

SEQUENCE LISTING

The instant application contains a Sequence Listing which has been filed electronically in ASCII format and is hereby incorporated by reference in its entirety. Said ASCII copy, created on Nov. 14, 2019, is named 60421-299807_SL.txt and is 972 bytes in size.

FIELD OF THE DISCLOSURE

The invention relates to direct-fed microbials for use in improving reproductive performance in animals, decreasing death loss and/or off-feed events in animals, improving milk production and/or milk quality in dairy animals, and inhibiting a disease or disorder in dairy animals selected from the group consisting of milk fever, ketosis, retained placenta, metritis, pneumonia, and displaced abomasum. More particularly, the invention relates to isolated *Bacillus* strains 86, 300, 101, 235, 177, and 102, and strains having all of the identifying characteristics of these strains, for uses comprising the above-mentioned uses.

BACKGROUND AND SUMMARY OF THE INVENTION

The present invention relates to direct-fed microbial (DFM) compositions. Reproductive performance is of high importance in all livestock production. In dairy cattle, rebreeding cows in a timely fashion is crucial to ensure that the cow will reach its potential in lifetime milk production. Delayed conception, high abortion rates, and low pregnancy rates can negatively affect a herd's total milk production, and cows with difficulties in reproduction often need to be removed from the herd. Improved reproductive performance creates value for a dairy in multiple ways: through increased milk production, through the additional calves that are born, and through the savings in replacement heifer costs. In addition, improved reproduction saves expenses associated with extra labor and technicians for inseminations, drugs for treatments, and the labor and costs of synchronization of time of insemination or ovulation.

Likewise, significant financial and labor investment is necessary in the rearing of livestock. Costs of feed, fresh water, shelter, vaccination and medical treatments, handling and milking are several of the significant expenses associated with managing livestock, including dairy cows. For example, costs of raising a single heifer replacement animal can exceed $1500. In the dairy industry, managing cow mortality is critical from both an economic and dairy animal welfare standpoint. Adult cow mortality has been rising in recent decades, and includes death losses from calving disorders, digestive disorders, locomotor disorders, metabolic disorders, udder/teat disorders, accidents and unknown causes. New technologies to lower death loss rates are needed in both the dairy industry and across the livestock industry as a whole.

As the world's population increases, the rising demand for high quality protein products, including dairy products, is rising, however, pressures to reduce the impact of farming on the environment through use of fewer land and water resources are also growing. Improvements in overall milk production per cow, and in milk components, including fat and protein help to fulfill both needs, meeting the rising requirement for greater dairy production without additional animal resources. In addition, efficient milk production is essential for the economic viability of a dairy. Boosting milk fat and protein percentages result in higher quality milk that generates greater revenue for a dairy.

Applicants have developed DFM compositions that result in improving reproductive performance in animals, decreasing death loss and/or off-feed events in animals, improving milk production and/or quality in dairy animals, and inhibiting a disease or disorder in dairy animals wherein the disease or disorder is selected from the group consisting of milk fever, ketosis, retained placenta, metritis, pneumonia, and displaced abomasum. The DFM compositions described herein offer a commercial benefit by providing all of these properties, or a combination thereof.

Methods and compositions are provided for improving reproductive performance in animals, decreasing death loss and/or off-feed events in animals, improving milk production and/or milk quality in dairy animals, and inhibiting a disease or disorder in dairy animals selected from the group consisting of milk fever, ketosis, retained placenta, metritis, pneumonia, and displaced abomasum. In various embodiments, the animal can be selected from the group consisting of a poultry species, a porcine species, a bovine species, an ovine species, an equine species, and a companion animal. In the embodiment where the animal is a porcine species, the porcine species can be selected from the group consisting of a grow finish pig, a nursery pig, a sow, and a breeding stock pig. In another embodiment, the animal can be a dairy animal selected from the group consisting of a cow, a goat, a sheep, or a buffalo.

In various embodiments, the compositions for use in the methods described herein can be a commercial package, a feed additive for an animal feed composition, an additive for the drinking water of an animal, or an animal feed composition (e.g., a complete feed), each comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

In another embodiment, a method of improving reproductive performance of an animal is provided. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain improves reproductive performance of the animal.

In yet another embodiment, a method of decreasing death loss and/or decreasing off-feed events for an animal is provided. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain decreases death loss and/or decreases off-feed events for the animal.

In still another embodiment, a method of improving milk production and/or milk quality in a dairy animal is provided. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain improves milk production and/or milk quality in the animal.

In another illustrative embodiment, a method of inhibiting a disease or disorder in dairy animals is provided, wherein the disease or disorder is selected from the group consisting of milk fever, ketosis, retained placenta, metritis, pneumonia, and displaced abomasum. The method can also be for other types of animals when the disease is pneumonia. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain inhibits the disease or disorder wherein the disease or disorder is selected from the group consisting of milk fever, ketosis, retained placenta, metritis, pneumonia, and displaced abomasum.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the EXAMPLES are applicable to any of the following embodiments of the invention described in the numbered clauses below.

1. A method of improving reproductive performance of an animal, the method comprising the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain improves reproductive performance of the animal.

2. A method of decreasing death loss and/or decreasing off-feed events for an animal, the method comprising the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain decreases death loss and/or decreases off-feed events for the animal.

3. The method of clause 1 or 2 wherein the animal is selected from the group consisting of a poultry species, a porcine species, a bovine species, an ovine species, an equine species, and a companion animal.

4. The method of any one of clauses 1 to 3 wherein the animal is a porcine species and the porcine species is selected from the group consisting of a grow finish pig, a nursery pig, a sow, and a breeding stock pig.

5. The method of clause 1 or 2 wherein the animal is a dairy animal.

6. The method of clause 5 wherein the dairy animal is selected from the group consisting of a cow, a goat, a sheep, or a buffalo.

7. The method of any one of clauses 1 to 6 wherein the Bacillus strain produces an enzyme selected from the group consisting of an α-galactosidase, a protease, a lipase, an amylase, a xylanase, a cellulase, and combinations thereof.

8. The method of any one of clauses 1 to 7 further comprising the step of administering to the animal another bacterial strain selected from the group consisting of another Bacillus strain, a lactic acid bacterial strain, and combinations thereof.

9. The method of any one of clauses 1 to 8 wherein Bacillus strain 86 (NRRL No. B-50944), Bacillus strain 300 (NRRL No. B-50943), Bacillus strain 101 (NRRL No. B-67218), Bacillus strain 235 (NRRL No. B-67219), Bacillus strain 177 (NRRL No. B-67275), and Bacillus strain 102 (NRRL No. B-67276) are all administered to the animal.

10. The method of any one of clauses 1 to 8 wherein the strain administered is Bacillus strain 101 (NRRL No. B-67218) or a strain having all of the identifying characteristics of Bacillus strain 101 (NRRL No. B-67218).

11. The method of any one of clauses 1 to 8 wherein the strain administered is Bacillus strain 235 (NRRL No. B-67219) or a strain having all of the identifying characteristics of Bacillus strain 235 (NRRL No. B-67219).

12. The method of any one of clauses 1 to 8 wherein the strain administered is Bacillus strain 86 (NRRL No. B-50944), or a strain having all of the identifying characteristics of Bacillus strain 86 (NRRL No. B-50944).

13. The method of any one of clauses 1 to 8 wherein the strain administered is Bacillus strain 300 (NRRL No. B-50943), or a strain having all of the identifying characteristics of Bacillus strain 300 (NRRL No. B-50943).

14. The method of any one of clauses 1 to 8 wherein the strain administered is Bacillus strain 177 (NRRL No. B-67275), or a strain having all of the identifying characteristics of Bacillus strain 177 (NRRL No. B-67275).

15. The method of any one of clauses 1 to 8 wherein the strain administered is Bacillus strain 102 (NRRL No. B-67276), or a strain having all of the identifying characteristics of Bacillus strain 102 (NRRL No. B-67276).

16. The method of any one of clauses 1 to 8 wherein the strain administered is Bacillus strain 101 (NRRL No. B-67218).

17. The method of any one of clauses 1 to 8 wherein the strain administered is Bacillus strain 235 (NRRL No. B-67219).

18. The method of any one of clauses 1 to 8 wherein the strain administered is Bacillus strain 86 (NRRL No. B-50944).

19. The method of any one of clauses 1 to 8 wherein the strain administered is Bacillus strain 300 (NRRL No. B-50943).

20. The method of any one of clauses 1 to 8 wherein the strain administered is Bacillus strain 177 (NRRL No. B-67275).

21. The method of any one of clauses 1 to 8 wherein the strain administered is Bacillus strain 102 (NRRL No. B-67276).

22. The method of any one of clauses 1 to 21 wherein each of the Bacillus strains is administered in the feed composition at a dose of about $1.0 \times 10^3$ CFU/pound of the feed composition to about $5.0 \times 10^{12}$ CFU/pound of the feed composition.

23. The method of any one of clauses 1 to 21 wherein each of the Bacillus strains is administered in the feed composition at a dose of about $0.5 \times 10^7$ CFU/pound of the feed composition to about $5.0 \times 10^7$ CFU/pound of the feed composition.

24. The method of any one of clauses 1 to 21 wherein each of the Bacillus strains is administered in the feed composition at a dose greater than about $5.0 \times 10^6$ CFU/pound of the feed composition.

25. The method of any one of clauses 1 to 24 further comprising the step of administering an antibiotic to the animal.

26. The method of clause 25 wherein the antibiotic is selected from the group consisting of erythromycin, levofloxacin, trimethoprim/sulfamethoxazole, trimethoprim, daptomycin, rifampicin, tylosin, tilmicosin, vancomycin, monensin, lasalocid, and laidlomycin propionate.

27. The method of any one of clauses 1 to 26 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

28. The method of clause 27 wherein the enzyme is an NSPase or a phytase.

29. The method of clause 1 or 2 wherein the animal is a cow and the Bacillus strain is administered during lactation.

30. The method of clause 1 or 2 wherein the animal is a cow and the Bacillus strain is administered during gestation.

31. The method of any one of clauses 1 to 30 wherein the feed composition is administered daily to the animal.

32. The method of any one of clauses 1 or 3 to 31 wherein the improvement in reproductive performance is selected from the group consisting of a decrease in the number of services to conception, an increase in heat detection, an increase in conception rate, a decrease in abortions, and an increase in pregnancy rate.

33. A method of improving milk production and/or milk quality in a dairy animal, the method comprising the step of administering to the animal a feed composition or drinking water comprising an effective amount of an additive comprising an isolated Bacillus strain selected from the group consisting of Bacillus strain 86 (NRRL No. B-50944), Bacillus strain 300 (NRRL No. B-50943), Bacillus strain 101 (NRRL No. B-67218), Bacillus strain 235 (NRRL No. B-67219), Bacillus strain 177 (NRRL No. B-67275), Bacillus strain 102 (NRRL No. B-67276), a strain having all of the identifying characteristics of Bacillus strain 86 (NRRL No. B-50944), a strain having all of the identifying characteristics of Bacillus strain 300 (NRRL No. B-50943), a strain having all of the identifying characteristics of Bacillus strain 101 (NRRL No. B-67218), a strain having all of the identifying characteristics of Bacillus strain 235 (NRRL No. B-67219), a strain having all of the identifying characteristics of Bacillus strain 177 (NRRL No. B-67275), a strain having all of the identifying characteristics of Bacillus strain 102 (NRRL No. B-67276), and combinations thereof, wherein the Bacillus strain improves milk production and/or milk quality in the animal.

34. A method of inhibiting a disease or disorder in a dairy animal wherein the disease or disorder is selected from the group consisting of milk fever, ketosis, retained placenta, metritis, pneumonia, and displaced abomasum, the method comprising the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain inhibits the disease or disorder in the dairy animal wherein the disease or disorder is selected from the group consisting of milk fever, ketosis, retained placenta, metritis, pneumonia, and displaced abomasum.

35. The method of clause 33 or 34 wherein the dairy animal is selected from the group consisting of a cow, a goat, a sheep, or a buffalo.

36. The method of any one of clauses 33 to 35 wherein the *Bacillus* strain produces an enzyme selected from the group consisting of an α-galactosidase, a protease, a lipase, an amylase, a xylanase, a cellulase, and combinations thereof.

37. The method of any one of clauses 33 to 36 further comprising the step of administering to the animal another bacterial strain selected from the group consisting of another *Bacillus* strain, a lactic acid bacterial strain, and combinations thereof.

38. The method of any one of clauses 33 to 37 wherein *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276) are all administered to the animal.

39. The method of any one of clauses 33 to 37 wherein the strain administered is *Bacillus* strain 101 (NRRL No. B-67218) or a strain having all of the identifying characteristics of *Bacillus* strain 101 (NRRL No. B-67218).

40. The method of any one of clauses 33 to 37 wherein the strain administered is *Bacillus* strain 235 (NRRL No. B-67219) or a strain having all of the identifying characteristics of *Bacillus* strain 235 (NRRL No. B-67219).

41. The method of any one of clauses 33 to 37 wherein the strain administered is *Bacillus* strain 86 (NRRL No. B-50944), or a strain having all of the identifying characteristics of *Bacillus* strain 86 (NRRL No. B-50944).

42. The method of any one of clauses 33 to 37 wherein the strain administered is *Bacillus* strain 300 (NRRL No. B-50943), or a strain having all of the identifying characteristics of *Bacillus* strain 300 (NRRL No. B-50943).

43. The method of any one of clauses 33 to 37 wherein the strain administered is *Bacillus* strain 177 (NRRL No. B-67275), or a strain having all of the identifying characteristics of *Bacillus* strain 177 (NRRL No. B-67275).

44. The method of any one of clauses 33 to 37 wherein the strain administered is *Bacillus* strain 102 (NRRL No. B-67276), or a strain having all of the identifying characteristics of *Bacillus* strain 102 (NRRL No. B-67276).

45. The method of any one of clauses 33 to 37 wherein the strain administered is *Bacillus* strain 101 (NRRL No. B-67218).

46. The method of any one of clauses 33 to 37 wherein the strain administered is *Bacillus* strain 235 (NRRL No. B-67219).

47. The method of any one of clauses 33 to 37 wherein the strain administered is *Bacillus* strain 86 (NRRL No. B-50944).

48. The method of any one of clauses 33 to 37 wherein the strain administered is *Bacillus* strain 300 (NRRL No. B-50943).

49. The method of any one of clauses 33 to 37 wherein the strain administered is *Bacillus* strain 177 (NRRL No. B-67275).

50. The method of any one of clauses 33 to 37 wherein the strain administered is *Bacillus* strain 102 (NRRL No. B-67276).

51. The method of any one of clauses 33 to 50 wherein each of the *Bacillus* strains is administered in the feed composition at a dose of about $1.0 \times 10^3$ CFU/pound of the feed composition to about $5.0 \times 10^{12}$ CFU/pound of the feed composition.

52. The method of any one of clauses 33 to 50 wherein each of the *Bacillus* strains is administered in the feed composition at a dose of about $0.5 \times 10^7$ CFU/pound of the feed composition to about $5.0 \times 10^7$ CFU/pound of the feed composition.

53. The method of any one of clauses 33 to 50 wherein each of the *Bacillus* strains is administered in the feed composition at a dose greater than about $5.0 \times 10^6$ CFU/pound of the feed composition.

54. The method of any one of clauses 33 to 53 further comprising the step of administering an antibiotic to the animal.

55. The method of clause 54 wherein the antibiotic is selected from the group consisting of erythromycin, levofloxacin, trimethoprim/sulfamethoxazole, trimethoprim, daptomycin, rifampicin, tylosin, tilmicosin, vancomycin, monensin, lasalocid, and laidlomycin propionate.

56. The method of any one of clauses 33 to 55 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

57. The method of clause 56 wherein the enzyme is an NSPase or a phytase.

58. The method of any one of clauses 33 to 57 wherein the *Bacillus* strain is administered during lactation.

59. The method of any one of clauses 33 to 57 wherein the *Bacillus* strain is administered during gestation.

60. The method of any one of clauses 33 to 59 wherein the feed composition is administered daily to the animal.

61. The method of any one of clauses 33 or 35 to 60 wherein the improvement in milk production and/or milk quality is selected from the group consisting of increasing milk production, increasing milk fat percentage, increasing milk protein, increasing overall fat corrected milk, increasing energy-corrected milk production, and decreasing somatic cell count.

62. The method of any one of clauses 1, 2, or 5 to 61 wherein the animal is a cow.

63. A commercial package for animal use comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

64. A feed additive for an animal feed comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

65. An additive for the drinking water of an animal comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

66. An animal feed composition comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

67. The commercial package, feed additive, additive for the drinking water of the animal, or animal feed composition of any one of clauses 63 to 66 for use in improving the reproductive performance of the animal.

68. The commercial package, feed additive, additive for the drinking water of the animal, or animal feed composition of any one of clauses 63 to 66 for use in decreasing death loss and/or off-feed events in the animal.

69. The commercial package, feed additive, additive for the drinking water of the animal, or animal feed composition of any one of clauses 63 to 66 for use in improving milk production and/or milk quality in the animal.

70. The commercial package, feed additive, additive for the drinking water of the animal, or animal feed composition of any one of clauses 63 to 66 for use in inhibiting a disease or disorder in the animal selected from the group consisting of milk fever, ketosis, retained placenta, metritis, pneumonia, and displaced abomasum.

71. The feed additive or additive for the drinking water of the animal of clause 64 or 65 in the form of a concentrate.

72. The feed additive or additive for the drinking water of the animal of clause 64 or 65 in the form of a superconcentrate.

73. The feed additive, the feed composition, or the additive for the drinking water of the animal of any one of clauses 64 to 72 in dry form.

74. The feed composition of clause 73 in pelleted form.

75. The commercial package, feed additive, or additive for the drinking water of the animal of any one of clauses 63 to 65 or 67 to 74 wherein the strains are in a form selected from the group consisting of a powder, a liquid, and a pellet form.

76. The commercial package, feed additive, additive for the drinking water of the animal, or feed composition of any one of clauses 63 to 75 further comprising a carrier for the *Bacillus* strains.

77. The commercial package, feed additive, additive for the drinking water of the animal, or feed composition of clause 76 wherein the carrier is selected from the group consisting of a bran, rice hulls, a salt, a dextrin, and combinations thereof.

78. The commercial package, feed additive, additive for the drinking water of the animal, or feed composition of any one of clauses 63 to 77 in a bag.

79. The commercial package, feed additive, additive for the drinking water of the animal, or feed composition of clause 78 wherein the bag is a plastic bag.

80. The commercial package, feed additive, additive for the drinking water of the animal, or feed composition of any one of clauses 63 to 79 further comprising instructions for use of one or more of the *Bacillus* strains.

81. The commercial package, feed additive, feed composition, or additive for the drinking water of the animal of any one of clauses 63 to 80 in a 20-pound bag.

82. The commercial package, feed additive, feed composition, or additive for the drinking water of the animal of any one of clauses 63 to 80 in a 50-pound bag.

83. The feed additive or additive for the drinking water of the animal of any one of clauses 64, 65, 67 to 73, or 75 to 82 in powder form.

84. The feed additive or additive for the drinking water of the animal of any one of clauses 64, 65, 67 to 72, 75, or 78 to 80 in liquid form.

85. The commercial package, feed additive, additive for the drinking water of the animal, or feed composition of any one of clauses 63 to 84 in a container for commercial use.

86. The commercial package, feed additive, additive for the drinking water of the animal, or feed composition of clause 85 wherein the container comprises plastic.

87. The commercial package, feed additive, additive for the drinking water of the animal, or feed composition of clause 85 wherein the container comprises paper.

88. The commercial package, feed additive, additive for the drinking water of the animal, or feed composition of any one of clauses 63 to 87 wherein the strains further comprise a binder.

89. The commercial package, feed additive, additive for the drinking water of the animal, or feed composition of clause 88 wherein the binder is selected from the group consisting of clay, yeast cell wall components, aluminum silicate, and glucan, or combinations thereof.

DETAILED DESCRIPTION OF ILLUSTRATIVE EMBODIMENTS

Figure 1:
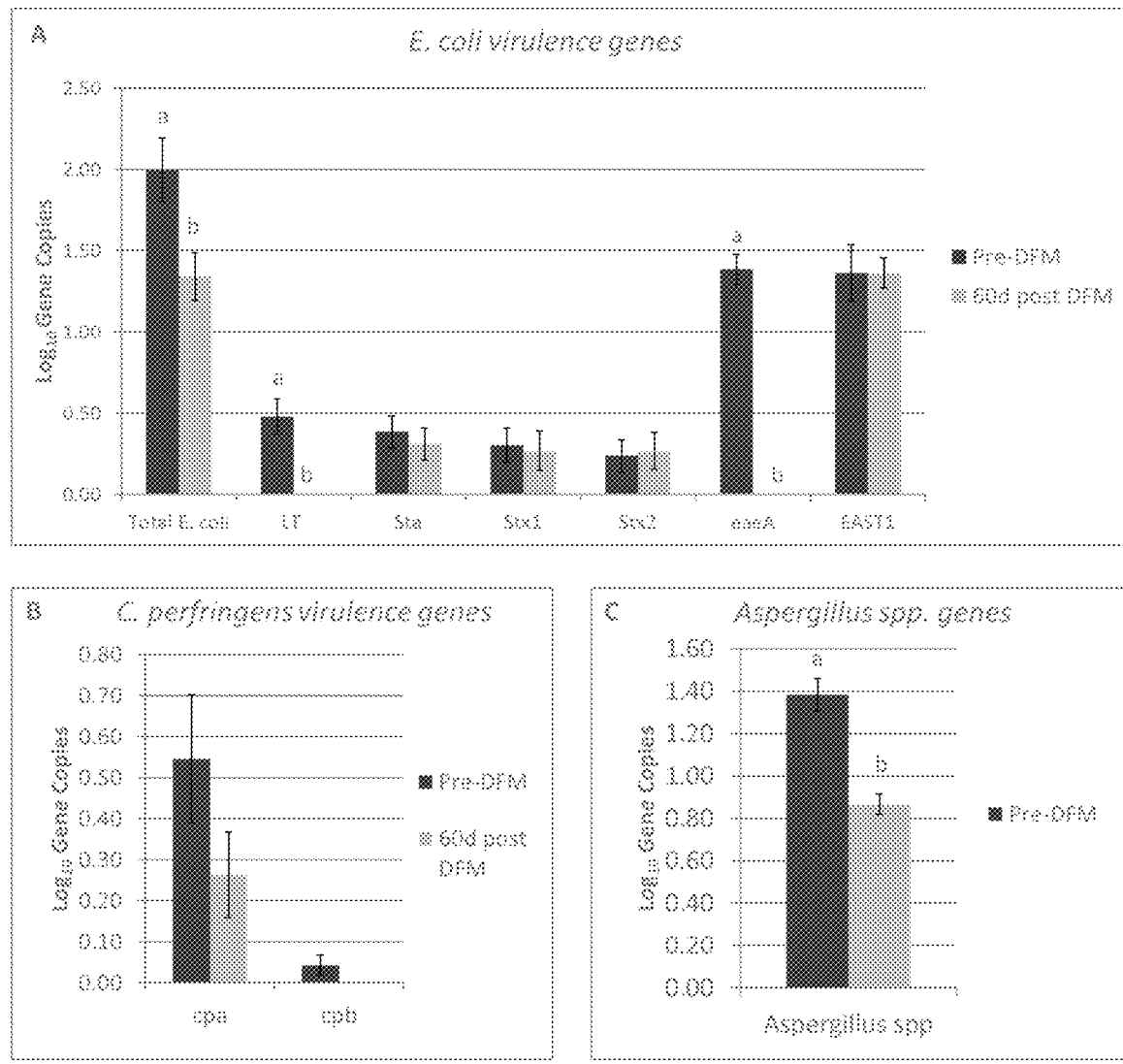
FIG. 1 is a graph showing (Panel A) reduction of rectal quantities of total *E. coli* (16S), the heat labile enterotoxin gene (LT), the intimin attaching and effacing gene (eaeA) of enteropathogenic and enterohemorrhagic *E. coli*, (Panel B) a numerical reduction in quantities of the *Clostridium perfringens* alpha and beta toxin genes (cpa and cpb respectively), and (Panel C) reduction in the *Aspergillus* (18S) gene ($p \leq 0.05$) during *Bacillus* supplementation.
Figure 2:
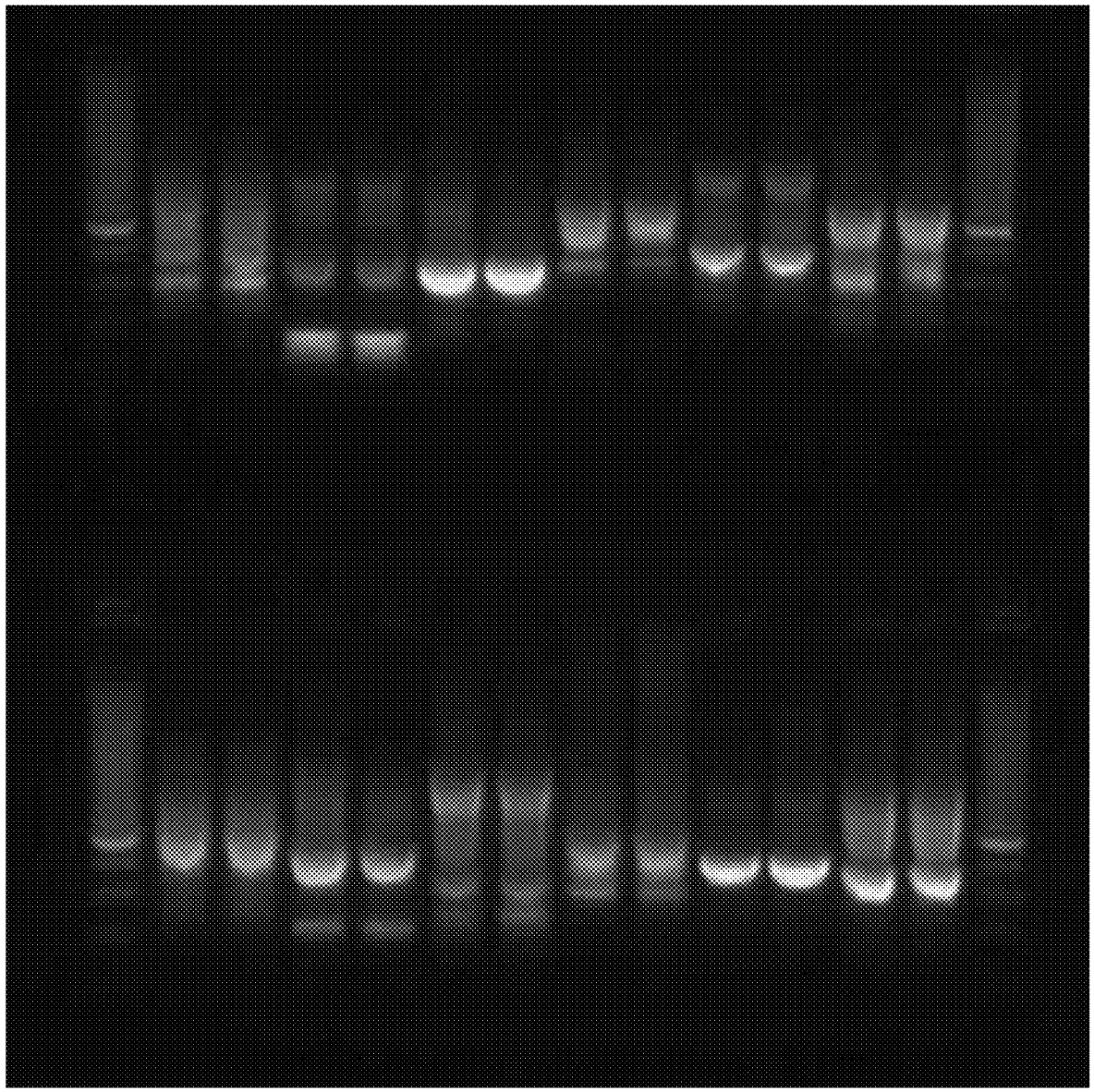
FIG. 2 shows a photograph of a gel displaying RAPD PCR profiles (Primer 1 to 6) for *Bacillus* strains 86 and 300. Strain 86 has the top profile and strain 300 has the bottom profile. The leftmost and rightmost lanes have markers and each set of two consecutive lanes between the markers corresponds to Primers 1 to 6 going from left to right.
Figure 3:
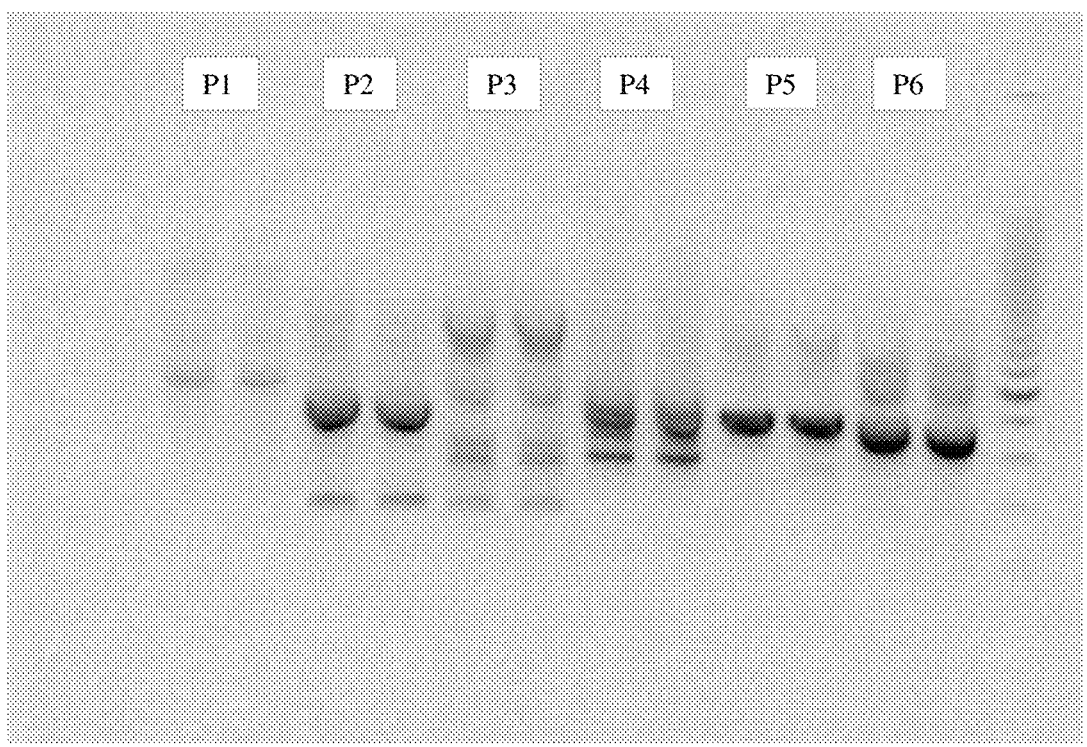
FIG. 3 shows a photograph of a gel displaying a RAPD PCR profile (Primer 1 to 6) for *Bacillus* strain 101. For Primer 1, faint bands appear at approximately 1000, 1500, and greater than 1600 base pairs. For Primer 2, an intense band appears at 650 base pairs and a faint band appears at approximately 400 base pairs. For Primer 3, a faint band appears at approximately 400 base pairs, a faint double band appears at 600 and 700 base pairs, and faint bands appear at 1000 and 1400 base pairs.
Figure 4:
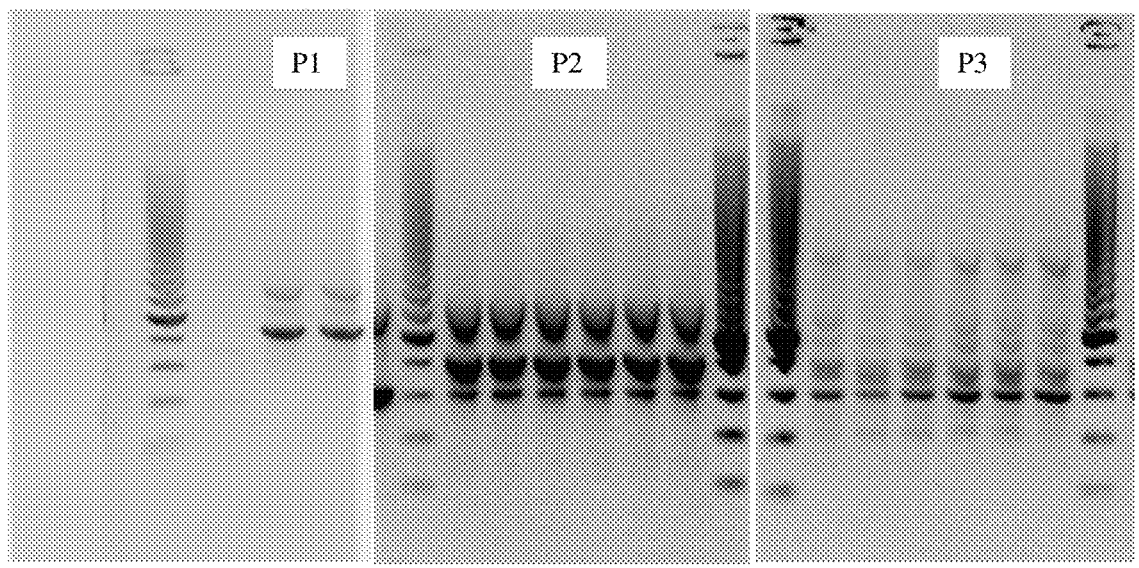
FIG. 4 shows a photograph of a gel displaying a RAPD PCR profile (Primer 1 to 3) for *Bacillus* strain 102. For Primer 1, an intense band appears at 900 base pairs and faint bands appear at 1200 and 1400 base pairs. For Primer 2, intense bands appear at 600, 700, and 1000 base pairs. For Primer 3, an intense band appears at 600 base pairs, double band at 700 and 750 base pairs, double band at 900 and 1100 base pairs, and faint bands appear at 400 and greater than 1800 base pairs.
Figure 5:
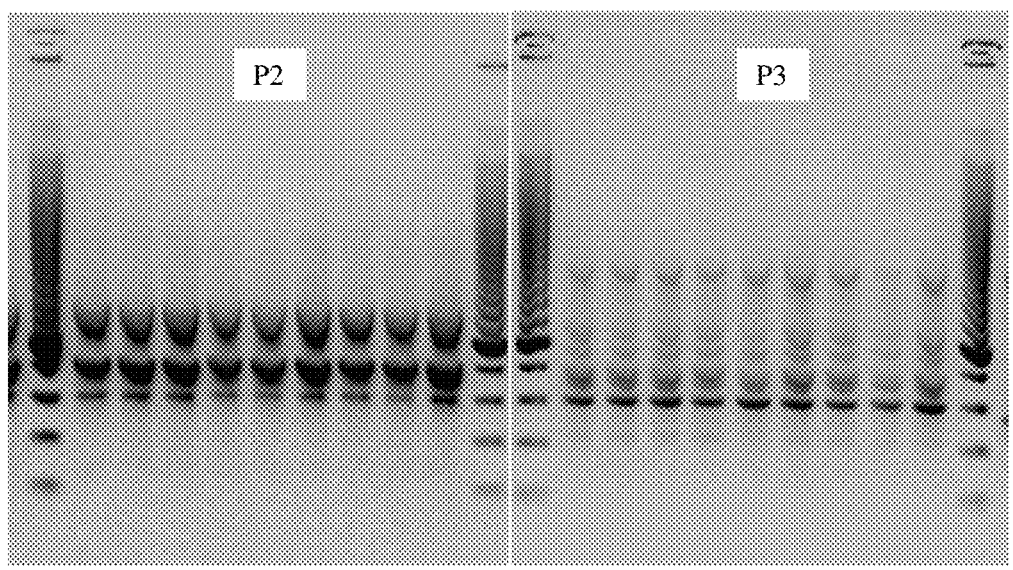
FIG. 5 shows a photograph of a gel displaying a RAPD PCR profile (Primer 2 and 3) for *Bacillus* strain 177. For Primer 2, intense bands appear at 600, 700, and 1000 base pairs. For Primer 3, intense bands appear at 600 base pairs, double band at 700 and 750 base pairs, double band at 900 and 1100 base pairs, and faint bands appear at 400 and greater than 1800 base pairs.
Figure 6:
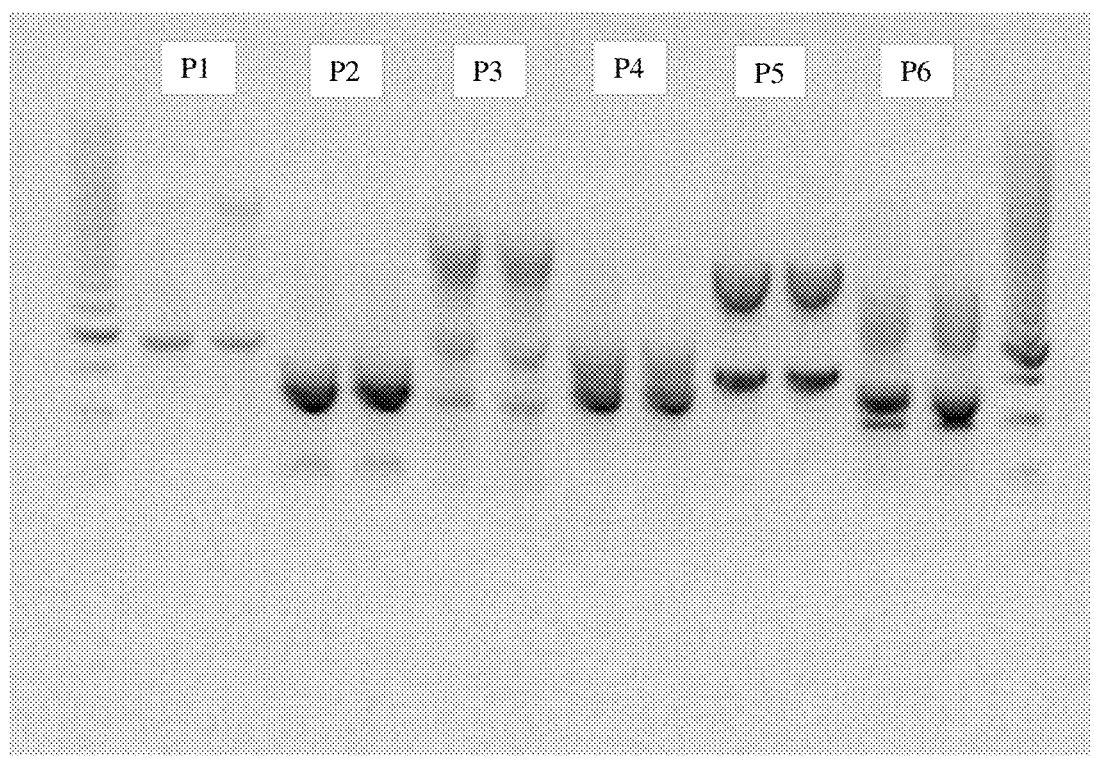
FIG. 6 shows a photograph of a gel displaying a RAPD PCR profile (Primer 1 to 6) for *Bacillus* strain 235. For Primer 1, faint bands appear at approximately 1000 and greater than 1600 base pairs. For Primer 2, an intense band appears at 650 base pairs and a faint band appears at approximately 400 base pairs. For Primer 3, faint bands appear at approximately 400, 600, 1000, and 1400 base pairs.

Methods and compositions are provided for improving reproductive performance in animals, decreasing death loss and/or off-feed events in animals, improving milk production and/or milk quality in dairy animals, and inhibiting a disease or disorder in dairy animals selected from the group consisting of milk fever, ketosis, retained placenta, metritis, pneumonia, and displaced abomasum. Methods are also provided for inhibiting pneumonia in animals described herein other than dairy animals. In various embodiments, the animal can be selected from the group consisting of a poultry species, a porcine species, a bovine species, an ovine species, an equine species, and a companion animal. In the embodiment where the animal is a porcine species, the porcine species can be selected from the group consisting of a grow finish pig, a nursery pig, a sow, and a breeding stock pig. In another embodiment, the animal can be a dairy animal selected from the group consisting of a cow, a goat, a sheep, or a buffalo.

In various embodiments, the compositions for use in the methods described herein can be a commercial package, a feed additive for an animal feed composition, an additive for the drinking water of an animal, or an animal feed composition (e.g., a complete feed), each comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

In another embodiment, a method of improving reproductive performance of an animal is provided. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain improves reproductive performance of the animal.

In yet another embodiment, a method of decreasing death loss and/or decreasing off-feed events for an animal is provided. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain decreases death loss and/or decreases off-feed events for the animal.

In still another embodiment, a method of improving milk production and/or milk quality in a dairy animal is provided. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain improves milk production and/or milk quality in the animal.

In another illustrative embodiment, a method of inhibiting a disease or disorder in dairy animals is provided, wherein the disease or disorder is selected from the group consisting of milk fever, ketosis, retained placenta, metritis, pneumonia, and displaced abomasum. The method comprises the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain inhibits the disease or disorder in dairy animals wherein the disease or disorder is selected from the group consisting of milk fever, ketosis, retained placenta, metritis, pneumonia, and displaced abomasum.

The following clauses, and combinations thereof, provide various additional illustrative aspects of the invention described herein. The various embodiments described in any other section of this patent application, including the section titled "BACKGROUND AND SUMMARY OF THE INVENTION" and the EXAMPLES are applicable to any of the following embodiments of the invention described in the numbered clauses below.

1. A method of improving reproductive performance of an animal, the method comprising the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain improves reproductive performance of the animal.

2. A method of decreasing death loss and/or decreasing off-feed events for an animal, the method comprising the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain decreases death loss and/or decreases off-feed events for the animal.

3. The method of clause 1 or 2 wherein the animal is selected from the group consisting of a poultry species, a porcine species, a bovine species, an ovine species, an equine species, and a companion animal.

4. The method of any one of clauses 1 to 3 wherein the animal is a porcine species and the porcine species is selected from the group consisting of a grow finish pig, a nursery pig, a sow, and a breeding stock pig.

5. The method of clause 1 or 2 wherein the animal is a dairy animal.

6. The method of clause 5 wherein the dairy animal is selected from the group consisting of a cow, a goat, a sheep, or a buffalo.

7. The method of any one of clauses 1 to 6 wherein the *Bacillus* strain produces an enzyme selected from the group consisting of an α-galactosidase, a protease, a lipase, an amylase, a xylanase, a cellulase, and combinations thereof.

8. The method of any one of clauses 1 to 7 further comprising the step of administering to the animal another bacterial strain selected from the group consisting of another *Bacillus* strain, a lactic acid bacterial strain, and combinations thereof.

9. The method of any one of clauses 1 to 8 wherein *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276) are all administered to the animal.

10. The method of any one of clauses 1 to 8 wherein the strain administered is *Bacillus* strain 101 (NRRL No. B-67218) or a strain having all of the identifying characteristics of *Bacillus* strain 101 (NRRL No. B-67218).

11. The method of any one of clauses 1 to 8 wherein the strain administered is *Bacillus* strain 235 (NRRL No. B-67219) or a strain having all of the identifying characteristics of *Bacillus* strain 235 (NRRL No. B-67219).

12. The method of any one of clauses 1 to 8 wherein the strain administered is *Bacillus* strain 86 (NRRL No. B-50944), or a strain having all of the identifying characteristics of *Bacillus* strain 86 (NRRL No. B-50944).

13. The method of any one of clauses 1 to 8 wherein the strain administered is *Bacillus* strain 300 (NRRL No. B-50943), or a strain having all of the identifying characteristics of *Bacillus* strain 300 (NRRL No. B-50943).

14. The method of any one of clauses 1 to 8 wherein the strain administered is *Bacillus* strain 177 (NRRL No. B-67275), or a strain having all of the identifying characteristics of *Bacillus* strain 177 (NRRL No. B-67275).

15. The method of any one of clauses 1 to 8 wherein the strain administered is *Bacillus* strain 102 (NRRL No. B-67276), or a strain having all of the identifying characteristics of *Bacillus* strain 102 (NRRL No. B-67276).

16. The method of any one of clauses 1 to 8 wherein the strain administered is *Bacillus* strain 101 (NRRL No. B-67218).

17. The method of any one of clauses 1 to 8 wherein the strain administered is *Bacillus* strain 235 (NRRL No. B-67219).

18. The method of any one of clauses 1 to 8 wherein the strain administered is *Bacillus* strain 86 (NRRL No. B-50944).

19. The method of any one of clauses 1 to 8 wherein the strain administered is *Bacillus* strain 300 (NRRL No. B-50943).

20. The method of any one of clauses 1 to 8 wherein the strain administered is *Bacillus* strain 177 (NRRL No. B-67275).

21. The method of any one of clauses 1 to 8 wherein the strain administered is *Bacillus* strain 102 (NRRL No. B-67276).

22. The method of any one of clauses 1 to 21 wherein each of the *Bacillus* strains is administered in the feed composition at a dose of about $1.0 \times 10^3$ CFU/pound of the feed composition to about $5.0 \times 10^{12}$ CFU/pound of the feed composition.

23. The method of any one of clauses 1 to 21 wherein each of the *Bacillus* strains is administered in the feed composition at a dose of about $0.5 \times 10^7$ CFU/pound of the feed composition to about $5.0 \times 10^7$ CFU/pound of the feed composition.

24. The method of any one of clauses 1 to 21 wherein each of the *Bacillus* strains is administered in the feed composition at a dose greater than about $5.0 \times 10^6$ CFU/pound of the feed composition.

25. The method of any one of clauses 1 to 24 further comprising the step of administering an antibiotic to the animal.

26. The method of clause 25 wherein the antibiotic is selected from the group consisting of erythromycin, levofloxacin, trimethoprim/sulfamethoxazole, trimethoprim, daptomycin, rifampicin, tylosin, tilmicosin, vancomycin, monensin, lasalocid, and laidlomycin propionate.

27. The method of any one of clauses 1 to 26 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

28. The method of clause 27 wherein the enzyme is an NSPase or a phytase.

29. The method of clause 1 or 2 wherein the animal is a cow and the *Bacillus* strain is administered during lactation.

30. The method of clause 1 or 2 wherein the animal is a cow and the *Bacillus* strain is administered during gestation.

31. The method of any one of clauses 1 to 30 wherein the feed composition is administered daily to the animal.

32. The method of any one of clauses 1 or 3 to 31 wherein the improvement in reproductive performance is selected from the group consisting of a decrease in the number of services to conception, an increase in heat detection, an increase in conception rate, a decrease in abortions, and an increase in pregnancy rate.

33. A method of improving milk production and/or milk quality in a dairy animal, the method comprising the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain improves milk production and/or milk quality in the animal.

34. A method of inhibiting a disease or disorder in a dairy animal wherein the disease or disorder is selected from the group consisting of milk fever, ketosis, retained placenta, metritis, pneumonia, and displaced abomasum, the method comprising the step of administering to the animal a feed composition or drinking water comprising an effective amount of an additive comprising an isolated *Bacillus* strain selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), a strain having all of the identifying characteristics of *Bacillus* strain 102 (NRRL No. B-67276), and combinations thereof, wherein the *Bacillus* strain inhibits the disease or disorder in the dairy animal wherein the disease or disorder is selected from the group consisting of milk fever, ketosis, retained placenta, metritis, pneumonia, and displaced abomasum.

35. The method of clause 33 or 34 wherein the dairy animal is selected from the group consisting of a cow, a goat, a sheep, or a buffalo.

36. The method of any one of clauses 33 to 35 wherein the *Bacillus* strain produces an enzyme selected from the group consisting of an α-galactosidase, a protease, a lipase, an amylase, a xylanase, a cellulase, and combinations thereof.

37. The method of any one of clauses 33 to 36 further comprising the step of administering to the animal another bacterial strain selected from the group consisting of another *Bacillus* strain, a lactic acid bacterial strain, and combinations thereof.

38. The method of any one of clauses 33 to 37 wherein *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276) are all administered to the animal.

39. The method of any one of clauses 33 to 37 wherein the strain administered is *Bacillus* strain 101 (NRRL No. B-67218) or a strain having all of the identifying characteristics of *Bacillus* strain 101 (NRRL No. B-67218).

40. The method of any one of clauses 33 to 37 wherein the strain administered is *Bacillus* strain 235 (NRRL No. B-67219) or a strain having all of the identifying characteristics of *Bacillus* strain 235 (NRRL No. B-67219).

41. The method of any one of clauses 33 to 37 wherein the strain administered is *Bacillus* strain 86 (NRRL No. B-50944), or a strain having all of the identifying characteristics of *Bacillus* strain 86 (NRRL No. B-50944).

42. The method of any one of clauses 33 to 37 wherein the strain administered is *Bacillus* strain 300 (NRRL No. B-50943), or a strain having all of the identifying characteristics of *Bacillus* strain 300 (NRRL No. B-50943).

43. The method of any one of clauses 33 to 37 wherein the strain administered is *Bacillus* strain 177 (NRRL No. B-67275), or a strain having all of the identifying characteristics of *Bacillus* strain 177 (NRRL No. B-67275).

44. The method of any one of clauses 33 to 37 wherein the strain administered is *Bacillus* strain 102 (NRRL No.

B-67276), or a strain having all of the identifying characteristics of *Bacillus* strain 102 (NRRL No. B-67276).

45. The method of any one of clauses 33 to 37 wherein the strain administered is *Bacillus* strain 101 (NRRL No. B-67218).

46. The method of any one of clauses 33 to 37 wherein the strain administered is *Bacillus* strain 235 (NRRL No. B-67219).

47. The method of any one of clauses 33 to 37 wherein the strain administered is *Bacillus* strain 86 (NRRL No. B-50944).

48. The method of any one of clauses 33 to 37 wherein the strain administered is *Bacillus* strain 300 (NRRL No. B-50943).

49. The method of any one of clauses 33 to 37 wherein the strain administered is *Bacillus* strain 177 (NRRL No. B-67275).

50. The method of any one of clauses 33 to 37 wherein the strain administered is *Bacillus* strain 102 (NRRL No. B-67276).

51. The method of any one of clauses 33 to 50 wherein each of the *Bacillus* strains is administered in the feed composition at a dose of about $1.0 \times 10^3$ CFU/pound of the feed composition to about $5.0 \times 10^{12}$ CFU/pound of the feed composition.

52. The method of any one of clauses 33 to 50 wherein each of the *Bacillus* strains is administered in the feed composition at a dose of about $0.5 \times 10^7$ CFU/pound of the feed composition to about $5.0 \times 10^7$ CFU/pound of the feed composition.

53. The method of any one of clauses 33 to 50 wherein each of the *Bacillus* strains is administered in the feed composition at a dose greater than about $5.0 \times 10^6$ CFU/pound of the feed composition.

54. The method of any one of clauses 33 to 53 further comprising the step of administering an antibiotic to the animal.

55. The method of clause 54 wherein the antibiotic is selected from the group consisting of erythromycin, levofloxacin, trimethoprim/sulfamethoxazole, trimethoprim, daptomycin, rifampicin, tylosin, tilmicosin, vancomycin, monensin, lasalocid, and laidlomycin propionate.

56. The method of any one of clauses 33 to 55 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

57. The method of clause 56 wherein the enzyme is an NSPase or a phytase.

58. The method of any one of clauses 33 to 57 wherein the *Bacillus* strain is administered during lactation.

59. The method of any one of clauses 33 to 57 wherein the *Bacillus* strain is administered during gestation.

60. The method of any one of clauses 33 to 59 wherein the feed composition is administered daily to the animal.

61. The method of any one of clauses 33 or 35 to 60 wherein the improvement in milk production and/or milk quality is selected from the group consisting of increasing milk production, increasing milk fat percentage, increasing milk protein, increasing overall fat corrected milk, increasing energy-corrected milk production, and decreasing somatic cell count.

62. The method of any one of clauses 1, 2, or 5 to 61 wherein the animal is a cow.

63. A commercial package for animal use comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

64. A feed additive for an animal feed comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

65. An additive for the drinking water of an animal comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

66. An animal feed composition comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

67. The commercial package, feed additive, additive for the drinking water of the animal, or animal feed composition of any one of clauses 63 to 66 for use in improving the reproductive performance of the animal.

68. The commercial package, feed additive, additive for the drinking water of the animal, or animal feed composition of any one of clauses 63 to 66 for use in decreasing death loss and/or off-feed events in the animal.

69. The commercial package, feed additive, additive for the drinking water of the animal, or animal feed composition of any one of clauses 63 to 66 for use in improving milk production and/or milk quality in the animal.

70. The commercial package, feed additive, additive for the drinking water of the animal, or animal feed composition of any one of clauses 63 to 66 for use in inhibiting a disease or disorder in the animal selected from the group consisting of milk fever, ketosis, retained placenta, metritis, pneumonia, and displaced abomasum.

71. The feed additive or additive for the drinking water of the animal of clause 64 or 65 in the form of a concentrate.

72. The feed additive or additive for the drinking water of the animal of clause 64 or 65 in the form of a superconcentrate.

73. The feed additive, the feed composition, or the additive for the drinking water of the animal of any one of clauses 64 to 72 in dry form.

74. The feed composition of clause 73 in pelleted form.

75. The commercial package, feed additive, or additive for the drinking water of the animal of any one of clauses 63 to 65 or 67 to 74 wherein the strains are in a form selected from the group consisting of a powder, a liquid, and a pellet form.

76. The commercial package, feed additive, additive for the drinking water of the animal, or feed composition of any one of clauses 63 to 75 further comprising a carrier for the *Bacillus* strains.

77. The commercial package, feed additive, additive for the drinking water of the animal, or feed composition of clause 76 wherein the carrier is selected from the group consisting of a bran, rice hulls, a salt, a dextrin, and combinations thereof.

78. The commercial package, feed additive, additive for the drinking water of the animal, or feed composition of any one of clauses 63 to 77 in a bag.

79. The commercial package, feed additive, additive for the drinking water of the animal, or feed composition of clause 78 wherein the bag is a plastic bag.

80. The commercial package, feed additive, additive for the drinking water of the animal, or feed composition of any one of clauses 63 to 79 further comprising instructions for use of one or more of the *Bacillus* strains.

81. The commercial package, feed additive, feed composition, or additive for the drinking water of the animal of any one of clauses 63 to 80 in a 20-pound bag.

82. The commercial package, feed additive, feed composition, or additive for the drinking water of the animal of any one of clauses 63 to 80 in a 50-pound bag.

83. The feed additive or additive for the drinking water of the animal of any one of clauses 64, 65, 67 to 73, or 75 to 82 in powder form.

84. The feed additive or additive for the drinking water of the animal of any one of clauses 64, 65, 67 to 72, 75, or 78 to 80 in liquid form.

85. The commercial package, feed additive, additive for the drinking water of the animal, or feed composition of any one of clauses 63 to 84 in a container for commercial use.

86. The commercial package, feed additive, additive for the drinking water of the animal, or feed composition of clause 85 wherein the container comprises plastic.

87. The commercial package, feed additive, additive for the drinking water of the animal, or feed composition of clause 85 wherein the container comprises paper.

88. The commercial package, feed additive, additive for the drinking water of the animal, or feed composition of any one of clauses 63 to 87 wherein the strains further comprise a binder.

89. The commercial package, feed additive, additive for the drinking water of the animal, or feed composition of clause 88 wherein the binder is selected from the group consisting of clay, yeast cell wall components, aluminum silicate, and glucan, or combinations thereof.

In various embodiments, the animal to which a feed additive, a feed composition, or drinking water as described herein is administered can be selected from the group consisting of a poultry species, a porcine species, a bovine species, an ovine species, an equine species, and a companion animal. In the embodiment where the animal is a companion animal, the companion animal can be, for example, a canine species or a feline species. In the embodiment where the animal is a porcine species, the porcine species can be selected from the group consisting of a grow finish pig, a nursery pig, a sow, and a breeding stock pig. In various exemplary embodiments, the animal can be selected from the group consisting of a chicken (e.g., a broiler or a layer), a pig, a horse, a pony, a cow, a buffalo, a turkey, a goat, a sheep, a quail, a pheasant, an ostrich, a duck, and combinations thereof. In one illustrative embodiment, the animal can be a cow.

In any embodiments described herein, except those requiring administering all of the strains in combination, the strains can be administered alone or in any combination. In one embodiment, an effective amount of the *Bacillus* strain can be administered to the animal. By "effective amount" is meant an amount of the *Bacillus* strain (e.g., strain 86, 300, 101, or 235, 177, or 102, or strains having all of their identifying characteristics) capable of improving reproductive performance in animals, decreasing death loss and/or off-feed events in animals, improving milk production and/or milk quality in dairy animals, and/or inhibiting a disease or disorder in dairy animals selected from the group consisting of milk fever, ketosis, retained placenta, metritis, pneumonia, and displaced abomasum, as described below, by any mechanism. In one aspect, the improvement in reproductive performance is selected from the group consisting of a decrease in the number of services to conception, an increase in heat detection rate, an increase in conception rate, a decrease in abortions, and an increase in pregnancy rate (e.g., a 21-day pregnancy rate). In another illustrative aspect, the improvement in milk production and/or milk quality is selected from the group consisting of increasing milk production, increasing milk fat percentage, increasing milk protein, increasing overall fat corrected milk, increasing energy-corrected milk production, and decreasing somatic cell count (for example, decreasing mean log somatic cell count).

As used herein, "inhibit a disease or disorder" can mean reducing the number of animals with the disease or disorder, preventing the disease or disorder, reducing the symptoms of the disease or disorder in animals, or combinations thereof, wherein the disease or disorder is selected from the group consisting of milk fever, ketosis, retained placenta, metritis, pneumonia, and displaced abomasum. As used herein, "decreasing death loss in animals" can mean reducing the number of losses of the animals by death or preventing losses of the animals by death. As used herein, "decreasing off-feed events in animals" can mean reducing the number of off-feed events in the animals or preventing any off-feed events in the animals or, for example, increasing daily rumination (e.g., time ruminating per day). As used herein, the terms "inhibit", "inhibiting", "inhibition", "decrease", "decreasing", "increase", "increasing", "improve", "improving", "improvement", "reduce", or "reducing" for example, are all relative to the condition of the animals (e.g., dairy animals) before administering the strain or strains to the animals (denominated "Pre-*Bacillus*" in the Examples) or, for example, relative to an animal not fed the *Bacillus* strain. As used herein "improving milk quality" can mean increasing milk fat percentage (or, for example, pounds of milk fat), increasing milk protein (for example, in percentage or pounds), increasing overall fat corrected milk, increasing energy-corrected milk production, and/or decreasing somatic cell count, as described herein. As used herein "energy-corrected milk" (ECM) is a calculation of the amount of energy in the milk based upon milk volume, fat and protein. Energy-corrected milk determines the amount of milk produced, adjusted to 3.5 percent fat and 3.2 percent protein. Energy-corrected milk is a more useful measurement to track herd productivity than simply volume of milk produced, as it puts all animals on an equal basis for comparative purposes over time.

In embodiments described herein wherein the compositions of the present invention comprising *Bacillus* strains 86, and/or 300, and/or 101, and/or 235, and/or 177, and/or 102, and/or strains having all of their identifying characteristics, are administered to an animal, the compositions are preferably administered to animals orally in a feed composition or in drinking water, but any other effective method of administration known to those skilled in the art may be utilized. In one illustrative embodiment, the *Bacillus* strains 86, and/or 300, and/or 101, and/or 235, and/or 177, and/or 102, and/or strains having all of their identifying characteristics, are provided in the form of an additive for addition to the drinking water of the animal.

In another illustrative embodiment, the *Bacillus* strains 86, and/or 300, and/or 101, and/or 235, and/or 177, and/or 102, and/or strains having all of their identifying characteristics, are provided in the form of a feed additive for addition to a feed composition. The feed composition may contain

*Bacillus* strain 86, and/or 300, and/or 101, and/or 235, and/or 177, and/or 102, and/or strains having all of their identifying characteristics, in a mixture with an animal feed blend, including any art-recognized animal feed blend or any animal feed blend described herein. As used herein, "feed composition" or "animal feed composition" means a feed composition comprising *Bacillus* strain 86, and/or 300, and/or 101, and/or 235, and/or 177, and/or 102, and/or strains having all of their identifying characteristics, in a mixture with an animal feed blend, and, optionally any other components that could be used in a feed composition, including other bacterial strains, such as other *Bacillus* strains or *Lactobacillus* strains.

Any animal feed blend, including those known in the art and those described herein, may be used in accordance with the methods and compositions described in this patent application, such as rapeseed meal, cottonseed meal, soybean meal, cornmeal, barley, wheat, silage, and haylage. In various embodiments, a corn silage and alfalfa hay-based total mixed ration or a corn silage mixed ration can be used. In various embodiments, the animal feed blend can be supplemented with *Bacillus* strain 86, and/or *Bacillus* strain 300, and/or *Bacillus* strain 101, and/or *Bacillus* strain 235, and/or *Bacillus* strain 177, and/or *Bacillus* strain 102, and/or strains having all of their identifying characteristics, but other ingredients may optionally be added to the animal feed blend, including other different bacterial strains, such as other *Bacillus* strains or *Lactobacillus* strains.

In various illustrative embodiments, optional ingredients of the animal feed blend include sugars and complex carbohydrates such as both water-soluble and water-insoluble monosaccharides, disaccharides, and polysaccharides. Other optional ingredients include dried distillers grain solubles, fat (e.g., crude fat), phosphorous, sodium bicarbonate, limestone, salt, phytate, calcium, sodium, sulfur, magnesium, potassium, copper, iron, manganese, zinc, ash, fish oil, an oil derived from fish meal, raw seed (e.g., flaxseed), an antioxidant, and starch. In another embodiment, minerals may be added in the form of a mineral premix.

Optional amino acid ingredients that may be added to the animal feed blend are arginine, histidine, isoleucine, leucine, lysine, cysteine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. In another embodiment, vitamins may be added in the form of a vitamin premix. In yet another embodiment, protein ingredients may be added to the animal feed blend and include protein obtained from meat meal, bone meal, or fish meal, liquid or powdered egg, fish solubles, crude protein, and the like.

In another illustrative aspect, any medicament ingredients known in the art may be added to the animal feed blend or to an additive for the drinking water of the animal, such as antibiotics. In various embodiments, the antibiotic is selected from the group consisting of erythromycin, levofloxacin, trimethoprim/sulfamethoxazole, trimethoprim, daptomycin, rifampicin, tylosin, tilmicosin, vancomycin, monensin, lasalocid, and laidlomycin propionate, and combinations thereof. In another embodiment, the animal feed blend, the feed composition, the feed additive, or the additive for the drinking water of the animal may contain antibiotics or may contain no antibiotics.

In another illustrative embodiment, one or more enzymes may be added to the animal feed blend. In various embodiments, the enzymes that may be added include a galactosidase, a phytase, a protease, a lipase, an amylase, a hemicellulase, an arabinoxylanase, a xylanase, a cellulase, an NSPase, combinations thereof, and any other enzyme that improves the effectiveness of the feed composition for the uses described herein. In yet another embodiment, yeast, fungi (e.g., *Aspergillus* or *Trichoderma*), or micronutrients may be added to the animal feed. Any of the ingredients described above that are suitable for addition to an additive for the drinking water of the animal may be added as a component of the additive for the drinking water of the animal as described herein.

In various illustrative embodiments, the *Bacillus* strain (e.g., *Bacillus* strain 86, and/or 300, and/or 101, and/or 235, and/or 177, and/or 102, and/or strains having all of their identifying characteristics), or any other different bacterial strains added in addition to these *Bacillus* strains, can be administered in the feed composition, each strain at a dose of about $1.0 \times 10^3$ CFU/pound of the feed composition to about $5.0 \times 10^{12}$ CFU/pound of the feed composition, each strain at a dose of about $0.5 \times 10^7$ CFU/pound of the feed composition to about $5.0 \times 10^7$ CFU/pound of the feed composition, or at a dose greater than about $5.0 \times 10^6$ CFU/pound of the feed composition. In other embodiments, each *Bacillus* strain (e.g., *Bacillus* strain 86, and/or 300, and/or 101, and/or 235, and/or 177, and/or 102, and/or strains having all of their identifying characteristics) can be administered in the feed composition at a dose greater than about $1.0 \times 10^3$ CFU/pound of the feed composition, at a dose greater than about $1.1 \times 10^3$ CFU/pound of the feed composition, at a dose greater than about $1.25 \times 10^3$ CFU/pound of the feed composition, at a dose greater than about $1.5 \times 10^3$ CFU/pound of the feed composition, at a dose greater than about $1.75 \times 10^3$ CFU/pound of the feed composition, at a dose greater than about $1.0 \times 10^4$ CFU/pound of the feed composition, at a dose greater than about $2.0 \times 10^4$ CFU/pound of the feed composition, at a dose greater than about $3.0 \times 10^4$ CFU/pound of the feed composition, at a dose greater than about $4.0 \times 10^4$ CFU/pound of the feed composition, at a dose greater than about $5.0 \times 10^4$ CFU/pound of the feed composition, at a dose greater than about $6.0 \times 10^4$ CFU/pound of the feed composition, at a dose greater than about $7.0 \times 10^4$ CFU/pound of the feed composition, at a dose greater than about $8.0 \times 10^4$ CFU/pound of the feed composition, at a dose greater than about $1.0 \times 10^5$ CFU/pound of the feed composition, at a dose greater than about $1.0 \times 10^6$ CFU/pound of the feed composition, at a dose greater than about $2.0 \times 10^6$ CFU/pound of the feed composition, at a dose greater than about $3.0 \times 10^6$ CFU/pound of the feed composition, at a dose greater than about $4.0 \times 10^6$ CFU/pound of the feed composition, at a dose greater than about $5.0 \times 10^6$ CFU/pound of the feed composition, at a dose greater than about $6.0 \times 10^6$ CFU/pound of the feed composition, at a dose greater than about $7.0 \times 10^6$ CFU/pound of the feed composition, at a dose greater than about $8.0 \times 10^6$ CFU/pound of the feed composition, at a dose greater than about $9.0 \times 10^6$ CFU/pound of the feed composition, at a dose greater than about $1.0 \times 10^7$ CFU/pound of the feed composition, at a dose greater than about $2.0 \times 10^7$ CFU/pound of the feed composition, at a dose greater than about $3.0 \times 10^7$ CFU/pound of the feed composition, at a dose greater than about $4.0 \times 10^7$ CFU/pound of the feed composition, at a dose greater than about $5.0 \times 10^7$ CFU/pound of the feed composition, at a dose greater than about $1.0 \times 10^8$ CFU/pound of the feed composition, at a dose greater than about $1.0 \times 10^9$ CFU/pound of the feed composition, at a dose greater than about $1.0 \times 10^{10}$ CFU/pound of the feed composition, at a dose greater than about $1.0 \times 10^{11}$ CFU/pound of the feed composition, or at a dose greater than about $1.0 \times 10^{12}$ CFU/pound of the feed composition. In all of the embodiments described in this paragraph, the animal can be fed, or can consume, about 30 pounds, about 35 pounds, about 40 pounds, about 45 pounds, about 50 pounds, about 55 pounds, about 60 pounds, about 65 pounds, or about 70 pounds of the feed composition per day.

In other embodiments, the *Bacillus* strains (e.g., *Bacillus* strain 86, 300, 101, 235, 177, and 102, and/or strains having all of their identifying characteristics), can be administered in the feed composition by adding about 15 grams of a feed additive to the complete feed composition wherein the 15 grams of the additive comprises all of the strains to provide a total of the combined strains in the 15 grams of the additive of about $1.0 \times 10^9$ CFU, about $2.0 \times 10^9$ CFU, about $3.0 \times 10^9$ CFU, about $4.0 \times 10^9$ CFU, about $5.0 \times 10^9$ CFU, about $6.0 \times 10^9$ CFU, about $7.0 \times 10^9$ CFU, about $8.0 \times 10^9$ CFU, about $9.0 \times 10^9$ CFU, or about $1.0 \times 10^{10}$ CFU to be fed to the animal per day. In all of the embodiments described in this paragraph, the animal can be fed, or can consume, about 30 pounds, about 35 pounds, about 40 pounds, about 45 pounds, about 50 pounds, about 55 pounds, about 60 pounds, about 65 pounds, or about 70 pounds of the complete feed composition per day, and the 15 grams of the feed additive can be added to any of these amounts of the feed composition.

In another embodiment, the *Bacillus* strains (e.g., *Bacillus* strain 86, 300, 101, 235, 177, and 102, and/or strains having all of their identifying characteristics), can be administered in the feed composition by adding about 15 grams of a feed additive comprising about $7.0 \times 10^9$ CFU total of the combined strains (e.g., about $7.35 \times 10^9$ CFU total) to, e.g., about 30 pounds, about 35 pounds, about 40 pounds, about 45 pounds, about 50 pounds, about 55 pounds, about 60 pounds, about 65 pounds, or about 70 pounds of the complete feed composition to be fed, or consumed, per animal per day.

In any of the dose embodiments for *Bacillus* strains 86, 300, 101, 235, 177, and 102, and/or strains having all of their identifying characteristics, described above, the *Bacillus* strains (*Bacillus* strain 86, 300, 101, 235, 177, and 102, and/or strains having all of their identifying characteristics) can be included in the feed additive, for addition to the feed composition, in exemplary ratios selected from any of the ratios shown below, wherein the ratios refer to the *Bacillus* strains 86, 300, 101, 235, 177, and 102, and/or strains having all of their identifying characteristics, in that order.

1:1:1:1:1:1
1:0.8:1:1:1:1
1:1:0.8:1:1:1
1:1:1:0.8:1:1
1:1:1:1:0.8:1
1:1:1:1:1:0.8
1:0.5:1:1:1:1
1:1:0.5:1:1:1
1:1:1:0.5:1:1
1:1:1:1:0.5:1
1:1:1:1:1:0.5
1:0.2:1:1:1:1
1:1:0.2:1:1:1
1:1:1:0.2:1:1
1:1:1:1:0.2:1
1:1:1:1:1:0.2
0.8:0.5:1:1:1:1
1:0.8:0.5:1:1:1
1:1:0.8:0.5:1:1
1:1:1:0.8:0.5:1
1:1:1:1:0.8:0.5
0.2:0.5:1:1:1:1
1:0.2:0.5:1:1:1
1:1:0.2:0.5:1:1
1:1:1:0.2:0.5:1
1:1:1:1:0.2:0.5
0.8:0.2:1:1:1:1
1:0.8:0.2:1:1:1
1:1:0.8:0.2:1:1
1:1:1:0.8:0.2:1
1:1:1:1:0.8:0.2
0.8:0.5:0.2:1:1:1
1:0.8:0.5:0.2:1:1
1:1:0.8:0.5:0.2:1
1:1:1:0.8:0.5:0.2
0.2:1:1:1:0.8:0.5
0.8:0.2:0.5:1:1:1
1:0.8:0.2:0.5:1:1
1:1:0.8:0.2:0.5:1
1:1:1:0.8:0.2:0.5
0.5:1:1:1:0.8:0.2
0.2:0.8::0.5:1:1:1
1:0.2:0.8:0.5:1:1
1:1:0.2:0.8:0.5:1
1:1:1:0.2:0.8:0.5
0.2:1:1:1:0.8:0.5

In various embodiments, the *Bacillus* strain (e.g., *Bacillus* strain 86, and/or 300, and/or 101, and/or 235, and/or 177, and/or 102) for use in accordance with the methods and compositions described herein can be selected from the group consisting of *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), *Bacillus* strain 102 (NRRL No. B-67276), a strain having all of the identifying characteristics of *Bacillus* strain 86 (NRRL No. B-50944), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 177 (NRRL No. B-67275), and a strain having all of the identifying characteristics of *Bacillus* strain 102 (NRRL No. B-67276). *Bacillus* strain MDG 101 and *Bacillus* strain MDG 235 were deposited on Jan. 4, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67218 and B-67219, respectively. *Bacillus* strain MGL177 and *Bacillus* strain MGL102 were deposited on Jun. 7, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67275 and B-67276, respectively. *Bacillus* strain MDG86 and *Bacillus* strain MDG300 were deposited on Mar. 14, 2014 at the Agricultural Research Service Culture Collection (NRRL), National Center for Agricultural Utilization Research, Agricultural Research Service, USDA, 1815 North University Street, Peoria, Illinois 61604-3999, and were given accession numbers B-50944 and B-50943, respectively. The NRRL strain designations MDG86 and MDG300 are equivalent to *Bacillus* strain 86 and 300, respectively, as referred to in the application. The NRRL strain designations MDG 101, MDG 235, MGL177, and MGL102 are equivalent to *Bacillus* strain 101, 235, 177, and 102 respectively, as referred to in the application. The deposits were made under the provisions of the Budapest Treaty on the International Recognition of the Deposit of Microorganisms for the Purposes of Patent Procedure. The strains described herein can be referred to as *Bacillus* strain 86, *Bacillus* strain 300, *Bacillus* strain 101, *Bacillus* strain 235, *Bacillus* strain 177, or *Bacillus* strain 102 or strain 86, strain 300, strain 101, strain 235, strain 177, or strain 102.

*Bacillus* strains 102 and 177 are *Bacillus pumilus* strains, *Bacillus* strain 77 is a *Bacillus licheniformis* strain, and all other strains described in the application are *Bacillus subtilus* strains.

Any of these strains can be administered alone or in combination in the form of a feed composition (e.g., a complete feed comprising an animal feed blend) or drinking water for an animal. In one embodiment, multiple strains are administered in combination in a single composition. In another embodiment, multiple strains are administered in separate compositions.

In another embodiment, one or more of the *Bacillus* strains described in the preceding paragraphs (e.g., *Bacillus* strain 86, and/or *Bacillus* strain 300, and/or *Bacillus* strain 101, and/or *Bacillus* strain 235, and/or *Bacillus* strain 177, and/or *Bacillus* strain 102, and/or strains having all of their identifying characteristics) can be administered to the animal along with another different bacterial strain selected from the group consisting of another *Bacillus* strain, a lactic acid bacterial strain, and combinations thereof. In yet another embodiment, one or more of the *Bacillus* strains described in the preceding paragraphs (e.g., *Bacillus* strain 86, and/or *Bacillus* strain 300, and/or *Bacillus* strain 101, and/or *Bacillus* strain 235, and/or *Bacillus* strain 177, and/or *Bacillus* strain 102, and/or strains having all of their identifying characteristics) can be administered to the animal along with any other different bacterial strain effective for the uses described herein.

As used herein "a strain having all of the identifying characteristics of" *Bacillus Bacillus* strain 86, *Bacillus* strain 300, *Bacillus* strain 101, *Bacillus* strain 235, *Bacillus* strain 177, or *Bacillus* strain 102 can be a mutant strain having all of the identifying characteristics of *Bacillus* strain 86, *Bacillus* strain 300, *Bacillus* strain 101, *Bacillus* strain 235, *Bacillus* strain 177, or *Bacillus* strain 102 (e.g., having a DNA fingerprint based on DNA analysis that corresponds to the DNA fingerprint of *Bacillus* strain 86, *Bacillus* strain 300, *Bacillus* strain 101, *Bacillus* strain 235, *Bacillus* strain 177, or *Bacillus* strain 102, enzyme activities that correspond to *Bacillus* strain 86, *Bacillus* strain 300, *Bacillus* strain 101, *Bacillus* strain 235, *Bacillus* strain 177, or *Bacillus* strain 102, antimicrobial activity that corresponds to *Bacillus* strain 86, *Bacillus* strain 300, *Bacillus* strain 101, *Bacillus* strain 235, *Bacillus* strain or 177, or *Bacillus* strain 102, antibiotic sensitivity and tolerance profiles that correspond to *Bacillus* strain 86, *Bacillus* strain 300, *Bacillus* strain 101, *Bacillus* strain 235, *Bacillus* strain 177, or *Bacillus* strain 102). In alternate embodiments, the mutation can be a natural mutation, or a genetically engineered mutation. In another embodiment, "a strain having all of the identifying characteristics of" *Bacillus* strain 86, *Bacillus* strain 300, *Bacillus* strain 101, *Bacillus* strain 235, *Bacillus* strain 177, or *Bacillus* strain 102 can be a strain, for example, produced by isolating one or more plasmids from *Bacillus* strain 86, *Bacillus* strain 300, *Bacillus* strain 101, *Bacillus* strain 235, *Bacillus* strain 177, or *Bacillus* strain 102 and introducing the one or more plasmids into another bacterium, such as another *Bacillus* strain, as long as the one or more plasmids contain DNA that provides the identifying characteristics of *Bacillus* strain 86, *Bacillus* strain 300, *Bacillus* strain 101, *Bacillus* strain 235, *Bacillus* strain 177, or *Bacillus* strain 102 (e.g., a DNA fingerprint based on DNA analysis that corresponds to the DNA fingerprint of *Bacillus* strain 86, *Bacillus* strain 300, *Bacillus* strain 101, *Bacillus* strain 235, *Bacillus* strain 177, or *Bacillus* strain 102).

The feed composition or drinking water comprising *Bacillus* strain 86, and/or *Bacillus* strain 300, and/or *Bacillus* strain 101, and/or *Bacillus* strain 235, and/or *Bacillus* strain 177, and/or *Bacillus* strain 102, and/or strains having all of their identifying characteristics, may be administered to the animal for any time period that is effective for the uses described herein, or combinations thereof. For example, in one embodiment the feed composition or drinking water may be provided to the animal daily. In an alternate embodiment, the feed composition or drinking water may be administered to the animal during lactation and/or during gestation. The time periods for administration of the feed composition or drinking water described above are non-limiting examples and it should be appreciated that any time period or administration schedule determined to be effective for the uses described herein, or combinations thereof, may be used.

In additional embodiments of the invention, compositions comprising *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, are provided. In one embodiment, a commercial package for animal use is provided comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

In another embodiment, a feed additive for an animal feed is provided comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

In yet another embodiment, an additive for the drinking water of an animal is provided comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

In still another embodiment, an animal feed composition is provided comprising all of the isolated strains comprising *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276).

In one embodiment, the feed additive for addition to an animal feed blend to produce a complete feed composition can be mixed with the animal feed blend, for example, with an automated micro-nutrient delivery system, or, for example, by hand-weighing and addition to achieve any of the doses of *Bacillus* strain 86, *Bacillus* strain 300, *Bacillus* strain 101, *Bacillus* strain 235, *Bacillus* strain 177, or *Bacillus* strain 102, and/or strains having all of their identifying characteristics, described herein, for administration to the animal in the form of a complete feed composition. The mixing can also be done by any other suitable method known in the art for combining direct-fed microbials with an animal feed blend to obtain a uniform mixture. In various embodiments, the mixing can be done for any suitable time period (e.g., about 1 to about 4 minutes). In the embodiment where *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, are in the form of an additive for the drinking water of the animal, *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, can be in the form of, for example, a powder, a liquid, or pellets, and can be mixed with the drinking water using any suitable method known in the art to achieve any of the doses of *Bacillus* strain 86, *Bacillus* strain 300, *Bacillus* strain 101, *Bacillus* strain 235, *Bacillus* strain 177, or *Bacillus* strain 102, and/or strains having all of their identifying characteristics, described herein, for administration to the animal in the drinking water of the animal. *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, can also be fed directly to the animal orally (i.e., by oral insertion) in the form of a powder, a liquid, a capsule, a top-dressing, a gel, or a pellet.

In any of the composition embodiments described herein, *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, can cause an effect selected from the group consisting of improving the reproductive performance of the animal, decreasing death loss and/or off-feed events in the animal, improving milk production and/or milk quality in the animal, and/or inhibiting a disease or disorder in the animal selected from the group consisting of milk fever, ketosis, retained placenta, metritis, pneumonia, and displaced abomasum.

In one illustrative aspect, the feed additive, additive for the drinking water of the animal, or the feed composition can be in the form of a commercial package. In another illustrative embodiment, the feed additive or additive for the drinking water of the animal comprising *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, in the commercial package can be in the form of a concentrate comprising, e.g., about $1 \times 10^8$ to about $7 \times 10^{10}$ CFU/g of the strains in combination, or a superconcentrate (e.g., about $8 \times 10^{10}$ to about $5 \times 10^{12}$ CFU/g of the strains in combination). In another embodiment, the feed additive, feed composition, or additive for the drinking water of the animal, or the *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, are in a composition in a commercial package, and can be in a dry form (e.g., a powder), a pelleted form, a liquid form, in the form of a top-dressing, or in the form of a gel, in the form of a capsule, or any other suitable form.

In yet another embodiment, the strains in the form of a commercial package can be, for example, in a dry form (e.g., a powder or freeze-dried form), in a pelleted form, or in a liquid form.

In another illustrative embodiment, the commercial package, feed additive, additive for the drinking water of the animal, or feed composition can further comprise a carrier for the *Bacillus* strain 86, *Bacillus* strain 300, *Bacillus* strain 101, *Bacillus* strain 235, *Bacillus* strain 177, and *Bacillus* strain 102, and/or strains having all of their identifying characteristics. The carrier can be selected from the group consisting of a bran, rice hulls, a salt, mineral oil, a dextrin (e.g., maltodextrin), whey, sugar, limestone, dried starch, sodium silico aluminate, vegetable oil, and combinations thereof. In another embodiment, the carrier can be any suitable carrier known in the art for a direct-fed microbial. In another embodiment, the commercial package, feed additive, additive for the drinking water of the animal, or feed composition can further comprise a binder such as clay, yeast cell wall components, aluminum silicate, glucan, or other known binders. In another embodiment, the commercial package, feed additive, additive for the drinking water of the animal, or feed composition can further comprise inorganic/organic binders, essential oils, and/or organic acids. Any of the binder or carrier components can be exogenously added (i.e., not naturally present in combination with the *Bacillus* strains) and any of the compositions described herein can be present in dietary nutrient compositions (e.g., probiotic compositions).

In yet other embodiments, the commercial package, feed additive, additive for the drinking water of the animal, or feed composition comprising *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, is in a container for commercial use. In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container for the commercial package, feed additive, additive for the drinking water of the animal, or feed composition comprising *Bacillus* strain 86, *Bacillus* strain 300, *Bacillus* strain 101, *Bacillus* strain 235, *Bacillus* strain 177, and *Bacillus* strain 102, and/or strains having all of their identifying characteristics, can comprise plastic, metal, foil, paper, fiber, or cardboard (e.g., a plastic pail, a paper bag, a foil bag, a fiber drum, etc.). The commercial package, feed additive, additive for the drinking water of the animal, or feed composition can further comprise instructions for use of one or more of the *Bacillus* strains.

In one aspect, any of the compositions described herein can further comprise an exogenously added (i.e., not naturally present with the *Bacillus* strain) nutrient component selected from the group consisting of a vitamin, an antibiotic, an enzyme, a water-soluble or water-insoluble monosaccharide, disaccharide, or polysaccharide, a fat, phosphorous, sodium bicarbonate, limestone, calcium, sodium, sulfur, magnesium, potassium, copper, iron, manganese, zinc, fish oil, raw seed, an antioxidant, and a starch. In one embodiment, the exogenously added nutrient component can be an enzyme and the enzyme can be selected from the group consisting of a galactosidase, a protease, a lipase, an amylase, a hemicellulase, an arabinoxylanase, a xylanase, a cellulase, an NSPase, a phytase, and combinations thereof.

The following examples are for illustrative purposes only. The examples are non-limiting, and are not intended to limit the invention in any way.

Example 1

Field Trial

The objective of the field trial was to determine the effect of supplementation with *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) on cow health, milk production, and reproduction parameters, on a 700-cow upper Midwest Holstein dairy farm with higher than average incidence of digestive issues.

Trial Design and Methods

Production, reproduction, and health metrics were monitored on the entire herd via Dairy Comp 305 (Valley Agricultural Software, Tulare, CA) with a period of 3 months pre-*Bacillus* supplementation serving as the baseline. The entire herd was then monitored for milk production, milk components, health, and reproductive performance for 10 months during which cows received daily *Bacillus* supplementation, measuring weekly individual cow milk production, monthly DHIA milk components, and monthly health events. During the *Bacillus* supplementation period, cows received 15 grams of the *Bacillus* product daily to provide $7.35 \times 10^9$ colony-forming units (CFU) per head per day of live *Bacillus* within a standard corn silage and alfalfa hay-based total mixed ration. Reproductive metrics were evaluated during a 6-month period over consecutive years, during which pre-*Bacillus* supplementation was compared to post-*Bacillus* supplementation to control for seasonal variation.

Statistical Analysis

Production and component data were analyzed by the MIXED procedure of SAS (version 9.2 SAS Institute, Cary N.C.) looking for fixed effects of treatment and the interaction of treatment*month*year, using days in milk (DIM) as covariate. Health and reproductive metrics were evaluated by the GLIMMIX procedure of SAS. Significance between means was defined at p≤0.05 and trends were indicated when p≤0.1.

Results

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) decreased incidence of displaced abomasum, ketosis, and metritis diseases in fresh cows.

TABLE 1

Treatment effect on mean percentage of fresh cows experiencing disease.

| | Pre-*Bacillus* | *Bacillus* | Treatment P-value |
|---|---|---|---|
| Displaced Abomasum | 12.68% | 4.72% | 0.0016 |
| Ketosis | 11.74% | 4.95% | <.0001 |
| Metritis | 12.68% | 5.29% | 0.0021 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) increased milk fat percentage and overall energy-corrected milk in the whole herd.

TABLE 2

Treatment effect on mean milk component percentages and daily energy-corrected milk production.

| | Pre-*Bacillus* | | *Bacillus* | | Treatment P-value |
|---|---|---|---|---|---|
| | LS Means | SEM | LS Means | SEM | |
| % Milk Fat | 4.0112% | 0.0198 | 4.2903% | 0.0098 | <0.0001 |
| % Milk Protein | 3.1543% | 0.00658 | 3.0892% | 0.003264 | <0.0001 |
| Energy Corrected Milk (lbs/cow/day) | 82.5794 | 0.5072 | 88.1808 | 0.2516 | <.0001 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) improved reproductive measures in the herd as evidenced by fewer services per conception, a higher heat detection, conception rate, and 21-day pregnancy rates.

TABLE 3

Treatment effect on reproductive efficiency metrics.

| | Pre-*Bacillus* | *Bacillus* | Treatment P-value |
|---|---|---|---|
| Heat Detection Rate, % | 52.6 | 57.3 | <0.05 |
| Services per Conception | 2.8 | 2.3 | <0.05 |
| Conception Rate, % | 36.0 | 43.8 | <0.05 |
| 21-Day Pregnancy Rate, % | 17.9 | 23.9 | <0.05 |

Example 2

Field Trial

The objective of the field trial was to determine the effect of supplementation with *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) on rectal microbial populations, cow health and milk production, on a 14,000-cow dairy in the Mountain-West region of the U.S. with higher than average incidence of digestive issues and a history of jejunal hemorrhagic syndrome.

Trial Design and Methods

The *Bacillus* direct-fed microbial was supplemented to cows on an Idaho dairy for a period of 6 months. During the *Bacillus* supplementation period, cows received 15 grams of the *Bacillus* product daily to provide $7.35 \times 10^9$ colony-forming units (CFU) per head per day of live *Bacillus* within a standard corn silage and alfalfa-haylage based total mixed ration. Prior to DFM supplementation, 40 randomly selected cows were sampled via rectal swabbing to establish baseline quantities of gastrointestinal-associated bacterial and fungal marker and virulence genes. Sampling was repeated 60 days after implementation of the *Bacillus* supplement, following the same host animals (n=37). Genomic DNA was isolated from fresh rectal swabs, quantified, and subjected to qPCR for quantification of target genes using primers and qPCR conditions referenced in Table 4.

TABLE 4

Microorganisms and associated gene targets measured by quantitative PCR (qPCR).

| Microorganism | Associated genes targets |
|---|---|
| E. coli | 16S rRNA: conserved gene in all E. coli |
|  | LT: Heat labile enterotoxin |
|  | Sta: Heat stable toxin A |
|  | eaeA: intimin adherence protein |
|  | stx1: Shiga toxin 1 |
|  | stx2: Shiga toxin 2 |
|  | EAST1: Enteroaggregative stable toxin |
| Clostridium perfringens | cpa: alpha toxin |
|  | cpb: beta toxin |
| Aspergillus spp. | 18S rRNA: conserved gene in all Aspergillus |

Production and health metrics were monitored on the entire herd via Dairy Comp 305 (Valley Agricultural Software, Tulare, CA) with a period of 6 months pre-*Bacillus* supplementation serving as the baseline. Then, for the next 6 months, the entire herd received daily *Bacillus* supplementation and was monitored for milk production and health events using weekly individual cow milk production and monthly health events. Milk fat and protein were evaluated monthly on a subset of cows (n=1055) during the same time period.

Statistical Analysis

Microbial gene quantities were $\log_{10}$ transformed and analyzed for significant effects of *Bacillus* treatment, using one-way ANOVA and Tukey pairwise comparisons in Minitab v.17 (State College, PA). Significance between means was defined at p≤0.05 and trends were indicated when p≤0.1. Production and component data were analyzed by the MIXED procedure of SAS (version 9.2 SAS Institute, Cary N.C.) looking for fixed effects of treatment and the interaction of treatment*month*year, using days in milk (DIM) as a covariate. Health and reproductive metrics were evaluated by the GLIMMIX procedure of SAS. Significance between means was defined at p≤0.05 and trends were indicated when p≤0.1.

Results

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) reduced gastrointestinal carriage of undesirable microbial populations. Specifically, longitudinal tracking of individual cows revealed that after 60 days of *Bacillus* supplementation there were significant reductions in rectal quantities of total *E. coli* (16S), the heat labile enterotoxin gene (LT), and the intimin attaching and effacing gene (eaeA) of enteropathogenic and enterohemorrhagic *E. coli*. Quantities of fungal *Aspergillus* (18S) gene were also reduced following supplementation (p<0.05), and quantities of the *Clostridium perfringens* alpha and beta toxin genes (cpa and cpb respectively) were numerically reduced during *Bacillus* supplementation (FIG. 1). Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) resulted in reduced incidence of milk fever (hypocalcemia) (Table 5) in fresh cows as well as a reduction in the number of cows in the entire herd off-feed (Table 5).

TABLE 5

Treatment effect on mean percentage of cows experiencing disease.

|  | Pre-*Bacillus* | *Bacillus* | Treatment P-value |
|---|---|---|---|
| Hypocalcemia (milk fever) | 2.37% | 1.69% | 0.0094 |
| Off-feed events per day | 545 | 357 | <.0001 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) resulted in significantly increased milk fat and protein percentages (Table 6) which, in turn, improved energy-corrected milk production (Table 6) compared to 6-month pre-*Bacillus* supplementation.

TABLE 6

Treatment effect on mean milk component percentages and daily energy-corrected milk production.

|  | Pre-*Bacillus* | | *Bacillus* | | Treatment P-value |
|---|---|---|---|---|---|
|  | LS Means | SEM | LS Means | SEM |  |
| % Milk Fat | 4.5393% | 0.0129 | 4.9569% | 0.0123 | <0.0001 |
| % Milk Protein | 3.4497% | 0.00497 | 3.5973% | 0.00471 | <0.0001 |
| Energy-Corrected Milk (lbs/cow/day) | 76.0631 | 0.2635 | 78.2249 | 0.2497 | <.0001 |

Example 3

Meta-Analysis of Five Field Trials

The objective of this study was to determine the effect of supplementation with *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) to five U.S. dairy herds, on transition cow health, herd death losses, abortion rate, milk quality, milk components, and milk production.

Trial Design and Methods

Production, reproduction, and health metrics were monitored on five herds representing 20,000 cows via Dairy Comp 305 (Valley Agricultural Software, Tulare, CA) or PCDART (DRMS, Raleigh, NC) software with a period of 3 months pre-*Bacillus* supplementation serving as the baseline. The herds were then monitored for 3 months during which cows received daily *Bacillus* supplementation, measuring weekly individual cow milk production, monthly DHIA milk components, and monthly health events. During the *Bacillus* supplementation period, cows received 15 grams of the *Bacillus* product daily to provide $7.35 \times 10^9$ colony-forming units (CFU) per head per day of live *Bacillus* within a corn-silage based total mixed ration.

Statistical Analysis

Milk production and component data were analyzed by the MIXED procedure of SAS, with fixed effects of treatment and the interaction of treatment*month*year, using days in milk and farm as covariates. Health and reproductive metrics were evaluated by the GLIMMIX procedure of SAS.

Results

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) resulted in significantly reduced incidence of retained placenta and ketosis, important health challenges in transition dairy cows (Table 7). Total herd death losses were also lower during the *Bacillus* supplementation period.

TABLE 7

Treatment effect on mean percentage of transition cow disease events and total herd death losses.

|  | Pre-*Bacillus* | | *Bacillus* | | |
| --- | --- | --- | --- | --- | --- |
|  | LS Means | SEM | LS Means | SEM | Treatment P-value |
| Retained Placenta | 13.54% | 0.97% | 9.74% | 0.91% | 0.0165 |
| Ketosis | 17.96% | 1.32% | 12.54% | 1.41% | 0.0157 |
| Metritis | 11.69% | 0.89% | 11.05% | 1.15% | 0.6640 |
| Displaced abomasum | 4.30% | 0.50% | 4.21% | 0.54% | 0.9078 |
| Death losses | 1.03% | 0.09% | 0.81% | 0.08% | 0.0918 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) resulted in significantly increased milk fat and protein percentages (Table 8). Energy-corrected milk production was increased by 2.47 pounds per cow per day during *Bacillus* consumption. In addition, somatic cell count, an indicator of bacterial infection of the mammary gland and a measure of milk quality, was also reduced during *Bacillus* supplementation (Table 8).

TABLE 8

Treatment effect on mean milk somatic cell count, milk component percentages and daily energy-corrected milk production.

|  | Pre-*Bacillus* | | *Bacillus* | | |
| --- | --- | --- | --- | --- | --- |
|  | LS Means | SEM | LS Means | SEM | Treatment P-value |
| Somatic Cell Count (in thousands of cells) | 438.01 | 10.985 | 404.26 | 10.693 | 0.0277 |
| % Milk Fat | 4.05 | 0.033 | 4.30 | 0.033 | <.0001 |
| % Milk Protein | 3.23 | 0.013 | 3.28 | 0.013 | 0.0079 |
| Energy Corrected Milk (lbs/cow/day) | 77.63 | 0.840 | 80.10 | 0.854 | 0.0387 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) improved reproductive measures in the herd as evidenced by fewer abortions (Table 9).

TABLE 9

Treatment effect on mean percentage of abortions.

|  | Pre-*Bacillus* | | *Bacillus* | | |
| --- | --- | --- | --- | --- | --- |
|  | LS Means | SEM | LS Means | SEM | Treatment P-value |
| Abortions | 4.11% | 0.31% | 3.14% | 0.22% | 0.0194 |

Example 4

RAPD (Randomly Amplified Polymorphic DNA) Analysis of DFM Strains

In order to obtain genetic barcodes or "fingerprints" of the *Bacillus* strains described herein, RAPD (randomly amplified polymorphic DNA) analysis was performed with each strain. Each isolate was cultured overnight in 10 ml of tryptic soy broth at 32° C. Thereafter, DNA was extracted from these cultures using Qiagen's DNeasy Mini kit, following the protocol provided for Gram-positive bacteria. A GE Healthcare Illustra Ready-To Go RAPD kit was used to perform RAPD-PCR with each DNA sample to amplify genetic fragments of arbitrary length. RAPD primers that were used for RAPD-PCR analysis include the following: Primer 1 (5'-GGTGCGGGAA-3') (SEQ ID NO: 1); PRIMER 2 (5'-GTTTCGCTCC3') (SEQ ID NO: 2); and PRIMER 3 (5'-GTAGACCCGT-3) (SEQ ID NO: 3). PCR products were separated via gel electrophoresis, and banding patterns were detected and matched using BioNumerics software. As shown in FIGS. 2 to 6, a common DNA fingerprint was not observed between the DFM strains. Therefore, FIGS. 2 to 6 demonstrate that the DFM strains described herein are different strains, each having a unique DNA fingerprint.

Example 5

Field Trial

The objective of this field trial was to determine the effect of supplementation with *Bacillus* strain 86 (NRRL No. B-50944). *Bacillus* strain 300 (NRRL No. R-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) on cow reproduction parameters, on a 870-cow central Texas Holstein dairy farm with average reproductive efficiency indicators.

Trial Design and Methods

Reproduction metrics were monitored on the entire herd via Dairy Comp 305 (Valley Agricultural Software, Tulare, CA). Cows received daily *Bacillus* supplementation at a rate of 7.5 grams of the *Bacillus* product to provide $3.68 \times 10^9$ colony-forming units (CFU) per head per day of live *Bacillus* within a standard corn silage, grass hay, and haylage-based total mixed ration. Conception rate, services per conception, 21-day pregnancy rate, and heat detection rate were calculated and measured during a 6-month period (November-April) following the start of the *Bacillus* supplementation. The same 6-month time-period (November-April) from the previous year was used as baseline (pre-*Bacillus* supplementation) to control for seasonal variation.

Statistical Analysis

Reproductive metrics were evaluated by the PROC MIXED procedure of SAS (version 9.2 SAS Institute, Cary NC). Significance between means was defined at p≤0.05 and trends were indicated when p≤0.1.

Results

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275) and *Bacillus* strain 235 (NRRL B-67219) improved reproductive measures in the herd as evidenced by fewer services per conception, a higher conception and 21-day pregnancy rates.

TABLE 10

Treatment effect on reproductive efficiency metrics

| | Pre-*Bacillus* | *Bacillus* | Treatment P-value |
|---|---|---|---|
| Heat detection rate, % | 57.1 | 61.8 | 0.1337 |
| Services per conception | 3.4 | 2.7 | 0.0003 |
| Conception rate, % | 29.7 | 37.8 | 0.0005 |
| 21-day pregnancy rate, % | 18.2 | 24.7 | 0.0104 |

Example 6

Field Trial

The objective of the field trial was to determine the effect of supplementation with *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) on cow health and milk production parameters on a 370-cow upper Midwest healthy Holstein dairy farm, with a few sporadic cases of hemorrhagic bowel syndrome (HBS).

Trial Design and Methods

Cows received daily *Bacillus* supplementation at a rate of 15 grams of the *Bacillus* product, corresponding at $7.35 \times 10^9$ colony-forming units (CFU) per head per day of live *Bacillus* within a standard corn silage and alfalfa hay-based total mixed ration. Production and health metrics were monitored on the entire herd via Dairy Comp 305 (Valley Agricultural Software, Tulare, CA). Milk production, milk components and health events data were collected 4 months pre-*Bacillus* supplementation, serving as the baseline, and 4 months following the start of the *Bacillus* supplementation. Rumination data was collected 5 months prior to the start of the *Bacillus* supplementation to serve as baseline and compared to 5 months post-*Bacillus* supplementation.

Statistical Analysis

Milk production and milk components data were analyzed using PROC MIXED of Statistical Analysis System (SAS) software, with Treatment*Month*Year and Treatment as main effects, using days in milk (DIM) as covariate. Health events data were analyzed using PROC GLIMMIX of SAS, with main effects of Treatment. Rumination data was analyzed by PROC MIXED, using Treatment as main effect and N as covariate. Significance between means was defined at p≤0.05 and trends were indicated when p≤0.1.

Results

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) for 4 months decreased the incidence of pneumonia in the whole herd.

TABLE 11

Treatment effect on mean percentage of fresh cows or whole herd experiencing pneumonia

| | | Pre-*Bacillus* | *Bacillus* | Treatment P-value |
|---|---|---|---|---|
| Pneumonia | Whole herd | 0.93% | 0.10% | 0.0190 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) increased daily rumination in whole herd.

TABLE 12

Treatment effect on mean rumination

| | Pre-*Bacillus* | | *Bacillus* | | |
|---|---|---|---|---|---|
| | LS Means | SEM | LS Means | SEM | Treatment P-value |
| Rumination (minutes/day) | 514.4 | 2.5157 | 530.8 | 2.491 | <.0001 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) increased milk production, milk fat percentage and pounds of milk fat and milk protein, resulting in increased overall fat corrected milk as well as energy corrected milk in the whole herd.

TABLE 13

Treatment effect on mean milk production, milk component percentages and daily energy-corrected milk production

| | Pre-*Bacillus* | | *Bacillus* | | |
|---|---|---|---|---|---|
| | LS Means | SEM | LS Means | SEM | Treatment P-value |
| Milk production (lbs/cow/day) | 62.935 | 0.4529 | 69.7133 | 0.449 | <.0001 |
| Energy Corrected Milk (lbs/cow/day) | 76.1103 | 0.5019 | 81.7609 | 0.5019 | <.0001 |
| Fat Corected Milk (lbs/cow/day) | 75.6833 | 0.5109 | 80.7342 | 0.5065 | <.0001 |
| Milk Fat, % | 4.8888 | 0.02086 | 4.5873 | 0.02068 | <.0001 |
| Milk Fat, lbs | 2.9937 | 0.02117 | 3.1235 | 0.02099 | <.0001 |
| Milk Protein, % | 3.5566 | 0.00799 | 3.5427 | 0.00792 | 0.2186 |
| Milk Protein, lbs | 2.1912 | 0.01419 | 2.4203 | 0.01407 | <.0001 |

Feeding *Bacillus* strain 86 (NRRL No. B-50944), *Bacillus* strain 300 (NRRL No. B-50943), *Bacillus* strain 101 (NRRL No. B-67218), *Bacillus* strain 102 (NRRL No. B-67276), *Bacillus* strain 177 (NRRL B-67275), and *Bacillus* strain 235 (NRRL B-67219) decreased log somatic cell count present in milk.

TABLE 14

Treatment effect on mean log somatic cell count

| | Pre-*Bacillus* | | *Bacillus* | | |
|---|---|---|---|---|---|
| | LS Means | SEM | LS Means | SEM | Treatment P-value |
| Log Somatic Cell Count | 158.44 | 9.9795 | 138.84 | 9.8849 | 0.1645 |

What is claimed is:

1. A method of improving reproductive performance of an animal being bred, the method comprising the step of administering to the animal being bred an effective amount of an additive in the feed composition or drinking water of said animal being bred, wherein said additive comprises the isolated strains *Bacillus* strain 86 (NRRL No. B-50944), *Bacillus* strain 300 (NRRL No. B-50943), *Bacillus* strain 101 (NRRL No. B-67218), *Bacillus* strain 235 (NRRL No. B-67219), *Bacillus* strain 177 (NRRL No. B-67275), and *Bacillus* strain 102 (NRRL No. B-67276), and improving reproductive performance of the animal being bred wherein the improvement in reproductive performance is selected from the group consisting of a decrease in the number of services to conception, an increase in heat detection, an increase in conception rate, a decrease in abortions, and an increase in pregnancy rate.

2. The method of claim 1 wherein the animal is selected from the group consisting of a poultry species, a porcine species, a bovine species, an ovine species, an equine species, and a companion animal.

3. The method of claim 1 wherein the animal is a porcine species and the porcine species is selected from the group consisting of a grow finish pig, a nursery pig, a sow, and a breeding stock pig.

4. The method of claim 1 wherein the animal is a dairy animal.

5. The method of claim 4 wherein the dairy animal is a cow.

6. The method of claim 1 wherein the *Bacillus* strain produces an enzyme selected from the group consisting of an α-galactosidase, a protease, a lipase, an amylase, a xylanase, a cellulase, and combinations thereof.

7. The method of claim 1 further comprising the step of administering to the animal another bacterial strain selected from the group consisting of another *Bacillus* strain, a lactic acid bacterial strain, and combinations thereof.

8. The method of claim 1 wherein each of the *Bacillus* strains is administered in the feed composition at a dose of about $1.0 \times 10^3$ CFU/pound of the feed composition to about $5.0 \times 10^{12}$ CFU/pound of the feed composition.

9. The method of claim 1 wherein each of the *Bacillus* strains is administered in the feed composition at a dose of about $0.5 \times 10^7$ CFU/pound of the feed composition to about $5.0 \times 10^7$ CFU/pound of the feed composition.

10. The method of claim 1 further comprising the step of administering an antibiotic to the animal.

11. The method of claim 10 wherein the antibiotic is selected from the group consisting of erythromycin, levofloxacin, trimethoprim/sulfamethoxazole, trimethoprim, daptomycin, rifampicin, tylosin, tilmicosin, vancomycin, monensin, lasalocid, and laidlomycin propionate.

12. The method of claim 1 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

13. The method of claim 12 wherein the enzyme is an NSPase or a phytase.

14. The method of claim 1 wherein the animal is a cow and the *Bacillus* strain is further administered during gestation and continued through lactation.

15. The method of claim 1 wherein the *Bacillus* strain is administered to the animal daily while the animal is being bred.

* * * * *